United States Patent
Yeh et al.

(10) Patent No.: US 7,588,927 B2
(45) Date of Patent: Sep. 15, 2009

(54) COMPOSITION AND METHODS RELATING TO SENP1—A SENTRIN-SPECIFIC PROTEASE

(75) Inventors: Edward T. H. Yeh, Houston, TX (US); Limin Gong, Pearland, TX (US)

(73) Assignees: National Institutes of Health (NIH), Washington, DC (US); The United States of America as represented by the Department of Health and Human Services, Washington, DC (US); U.S. Government NIH Divisional of Extramural Inventions and Technology Resources (DEITR), Washington, DC (US)

( * ) Notice: Subject to any disclaimer, the term of this patent is extended or adjusted under 35 U.S.C. 154(b) by 266 days.

(21) Appl. No.: 10/624,945

(22) Filed: Jul. 22, 2003

(65) Prior Publication Data

US 2006/0134741 A1    Jun. 22, 2006

Related U.S. Application Data

(63) Continuation of application No. 09/628,966, filed on Jul. 31, 2000, now Pat. No. 6,596,527.

(60) Provisional application No. 60/146,774, filed on Jul. 31, 1999.

(51) Int. Cl.
*C12N 9/64*  (2006.01)
*C12N 15/57*  (2006.01)
*C12N 15/85*  (2006.01)

(52) U.S. Cl. .................. 435/226; 435/69.1; 435/252.3; 435/320.1; 536/23.2

(58) Field of Classification Search .................. None
See application file for complete search history.

(56) References Cited

U.S. PATENT DOCUMENTS

| | | | | |
|---|---|---|---|---|
| 6,222,029 | B1 * | 4/2001 | Edwards et al. | 536/24.1 |
| 6,596,527 | B1 * | 7/2003 | Yeh et al. | 435/226 |
| 6,872,551 | B2 * | 3/2005 | Lima et al. | 435/69.7 |
| 2002/0106373 | A1 * | 8/2002 | Hillman et al. | 424/145.1 |
| 2002/0127692 | A1 * | 9/2002 | Ink et al. | 435/226 |
| 2003/0138839 | A1 * | 7/2003 | Li et al. | 435/7.1 |

(Continued)

FOREIGN PATENT DOCUMENTS

WO    WO 98/20038    5/1998

(Continued)

OTHER PUBLICATIONS

GenBank Accession No. AA236084, 1997, "zs05b06.r1 NCI_CGAP_GCB1 *Homo sapiens* cDNA clone Image:684275 5', mRNA sequence", National Cancer Institute, Cancer Genome Anatomy Project Tumor Gene Index.*

(Continued)

*Primary Examiner*—Rebecca E Prouty
*Assistant Examiner*—William W Moore
(74) *Attorney, Agent, or Firm*—Fulbright & Jaworski, L.L.P.

(57) ABSTRACT

The invention relates to a novel protease, called SENP1, which is active against sentrin-modified proteins in vivo. The invention more specifically relates to the genomic and amino acid sequences for SENP1, compositions related to and based on these sequences, and methods of using these sequences and compositions.

3 Claims, 10 Drawing Sheets

Activation    Conjugation    Sentrinization    De-sentrinization

Sentrinization and de-sentrinization pathway.

U.S. PATENT DOCUMENTS

2006/0057623 A1* 3/2006 Yeh .......................... 435/6

FOREIGN PATENT DOCUMENTS

WO    WO 98/56918    12/1998
WO    WO 00/78934    * 12/2000

OTHER PUBLICATIONS

GenBank Accession No. AA330056, 1997, "EST33924 Embryo, 12 week II *Homo sapiens* cDNA 5' end, mRNA sequence", The Institute for Genomic Research Human Gene Index and Adams, M.D., et al., 1995, Nature, vol. 377 (6547 Suppl), pp. 3-174.*

Sequence comparison: Seq ID No. 3 of U.S. Appl. No. 09/069,725 (Hillman et al.) with Seq ID No. 10 of U.S. Appl. No. 10/624,945.*

Gong et al., "Molecular cloning and characterization of human AOS1 and UBA2, components of the sentrin-activating enzyme complex," *FEBS Letter*, 448:185-189, 1999.

Gong et al., "Preferential interaction of sentrin with ubiquitin-conjugating enzyme, Ubc9," *J. Biol. Chem.*, 272:28198-28201, 1997.

Hershko and Ciechanover, "The Ubiquitin system," *Annu. Rev. Biochem.*, 67:425-479, 1998.

Kamitani et al., "Preferential modification of nuclear proteins by a novel ubiquitin-like molecule," *J. Biol. Chem.*, 272:14001-14004, 1997.

Kamitani et al., "Characterization of NEDD8, a developmentally down-regulated ubiquitin-like protein," *J. Biol. Chem.*, 272:28557-28562, 1997.

Kamitani et al., "Identification of three major sentrinization sites in PML," *J. Biol. Chem.*, 273:26675-26682, 1998.

Kamitani et al., "Covalent modification of PML by the sentrin family of ubiquitin-lik protein," *J. Biol. Chem.*, 273:3117-3120, 1998.

Kamitani et al., "Characterization of a second member of the sentrin family of ubiquitin-like proteins," *J. Biol. Chem.*, 274:11349-11353, 1998.

Li and Hochstrasser, "A new protease requried for cell-cycle progression in yeast," *Nature* 398:246-251, 1999.

Mahajan et al., "A small ubiquitin-related polypeptide involved in targeting RanGAP1 to nuclear pore complex protein RanBP2," *Cell*, 88:97-107, 1997.

Mahajian et al., "Molecular characterization of the SUMO-1 modification of RanGAP1 and its role in nuclear envelope association," *J. Cell Biol.*, 140:259-270, 1998.

Mao et al., "SUMO-1 conjugation to human DNA topoisomerase II isozymes," *J Biol Chem.*, 275:26066-26073, 2000.

Mao et al., "SUMO-1 conjugation to topoisomerase I: a possible repair response to topoisomerase-mediated DNA damage," *Proc Natl Acad Sci U S A*. 97:4046-4051, 2000.

Matunis et al., "SUMO-1 modification and its role in targeting the Ran GRPase-activating protein, RanGAP1, to the nuclear pore complex," *J. Cell Biol.* 140, 499-509, 1998.

Matunis, et al., "A novel ubiquitin-like modification modulates the partritioning of the Ran-GTPase-activating protein RanGAP1 between the cytosol and the nuclear pore complex," *J. Cell Biol.*, 135:1457-1470, 1996.

Nagase et al., "Prediction of the coding sequences of unidentified human genes. XVI. The complete sequences of 150 new cDNA clones from brain which code for large proteins in vitro," *DNA Research*, 7:65-73, 2000.

Okura et al., "Protection against Fas/AP0-1- and tumor necrosis factor-mediated cell death by a novel protein, sentrin," *J. Immunol.*, 157, 4277-4281, 1996.

Rangasamy et al., "SUMO-1 modification of bovine papillomavirus E1 protein is required for intranuclear accumulation," *J. Biol. Chem.*, 275:37999-38004, 2000.

Saitoh et al., "Ubc9p and the conjugation of SUMO-1 to RanGAP1 and Ran BP2," *Current Biol.*, 8:121-124, 1998.

Sternsdorf et al., "Evidence for covalent modification of the nuclear Dot-associated proteins PML and Sp100 by PIC1/SUM0-1," *J. Cell Biol.*, 139:1621-1634, 1997.

Wilkinson, "Regulation of ubiquitin-dependent processes by deubiquitinating enzymes," *FASEB J.*, 11:1245-1256, 1997.

Yeh et al., "Ubiquitin-like proteins: new wines in new bottles," *Gene*, 248:1-14, 2000.

Boddy et al., "PIC 1, a novel ubiquitin-like protein which interacts with the PML component of a multiprotein complex that is disrupted in acute promyelocytic leukaemia," *Oncogene*, 13:971-982, 1996.

Buschmann et al., "SUMO-1 modification of Mdm2 prevents its self-ubiquitination and increases Mdm2 ability to ubiquitinate p53," *Cell*. 101:753-762, 2000.

Database EMBL: HS 1154303, "zs05b06.s1 NCI_CGAP_GCB1 *Homo sapiens* cDNA clone Image:684275 3," 1997.

Database EMBL: HSM800198, "*Homo sapiens* mRNA; cDNA DKFZp586K0919 (from clone (DKFZp586K0919), complete cDNA," 1999.

den Dunnen, "Cosmied-based exon trapping," *Methods Enzymol.*, 303:100-110, 1999.

Desterro et al., "SUMO-1 modification of 1κα inhibits NF-κB activation," *Mol. Cell*, 2:233-239, 1998.

Gong and Yeh, "Identification of the activating and conjugating enzymes of the NEDD8 conjugation pathway," *J. Biol. Chem.*, 274:12036-12042, 1999.

Gong et al., "Differential regulation of sentrinized proteins by a novel sentrin-specific protease," *J. Biol. Chem.*, 275:3355-3359, 2000.

* cited by examiner

FIG. 1. Sentrinization and de-sentrinization pathway.

FIG. 2

```
   1  acctagcgactcttccggtgctgtgaaggcggttccggttcgcggcggttcccgggtttt
  61  gcgttccgcgcccggccggaaaccccttcgcatggcagccggttccggttcggactttgt
 121  atctttgctaaagtcagtgatgtgaaaagacttgaaatggatgatattgctgataggatg
                                          M  D  D  I  A  D  R  M       8
 181  aggatggatgctggagaagtgactttagtgaaccacaactccgtattcaaaacccacctc
      R  M  D  A  G  E  V  T  L  V  N  H  N  S  V  F  K  T  H  L      28
 241  ctgccacaaacaggttttccagaggaccagcttctgctttctgaccagcagattttatct
      L  P  Q  T  G  F  P  E  D  Q  L  S  L  S  D  Q  Q  I  L  S      48
 301  tccaggcaaggacatttggaccgatcttttacatgttccacaagaagtgcagcttataat
      S  R  Q  G  H  L  D  R  S  F  T  C  S  T  R  S  A  A  Y  N      68
 361  ccaagctattactcagataatccttcctcagacagttttcttggctcaggcgatttaaga
      P  S  Y  Y  S  D  N  P  S  S  D  S  F  L  G  S  G  D  L  R      88
 421  acctttggccagagtgcaaatggccaatggagaaattctaccccatcgtcaagctcatct
      T  F  G  Q  S  A  N  G  Q  W  R  N  S  T  P  S  S  S  S  S     108
 481  ttacaaaaatcaagaaacagccgaagtctttacctcgaaacccgaaagacctcaagtgga
      L  Q  K  S  R  N  S  R  S  L  Y  L  E  T  R  K  T  S  S  G     128
 541  ttatcaaacagtttgcgggaaagtcaaaccatcactgccatgtatctgcatatgaaaaa
      L  S  N  S  F  A  G  K  S  N  H  H  C  V  S  A  Y  E  K       148
 601  tcttttcctattaaacctgttccaagtccatcttggagtggttcatgtcgtcgaagtctt
      S  F  P  I  K  P  V  P  S  P  S  W  S  G  S  C  R  R  S  L     168
 661  ttgagccccaagaaaactcagaggcgactagtacagcagaagagacagttcaagaa
      L  S  P  K  K  T  Q  R  R  H  V  S  T  A  E  E  T  V  Q  E     188
 721  gaagaaagagagatttacagacagctgctacagatggtcacagggaaacagtttactata
      E  E  R  E  I  Y  R  Q  L  L  Q  M  V  T  G  K  Q  F  T  I     208
 781  gccaaacccaccacacattttcctttacacctgtctcgatgtcttagttccagtaaaaat
      A  K  P  T  T  H  F  P  L  H  L  S  R  C  L  S  S  K  N       228
 841  actttgaaagactcactgtttaaaaatggaaactcttgtgcatctcagatcattggctct
      T  L  K  D  S  L  F  K  N  G  N  S  C  A  S  Q  I  I  G  S     248
 901  gatacttcatcatctggatctgccagcatttaactaaccaggaacagctgtcccacagt
      D  T  S  S  S  G  S  A  S  I  L  T  N  Q  E  Q  L  S  H  S     268
 961  gtatattccctatcttcttataccccagatgttgcatttggatccaaagattctggtact
      V  Y  S  L  S  S  Y  T  P  D  V  A  F  G  S  K  D  S  G  T     288
1021  cttcatcatccccatcatcaccactctgttccacatcagccagataacttagcagcttca
      L  H  H  P  H  H  H  H  S  V  P  H  Q  P  D  N  L  A  A  S     308
1081  aatacacaatctgaaggatcagactctgtgattttactgaaagtgaaagattcccagact
      N  T  Q  S  E  G  S  D  S  V  I  L  L  K  V  K  D  S  Q  T     328
1141  ccaactcccagttctactttcttccaggcagagctgtggatcaaagaattaactagtgtt
      P  T  P  S  S  T  F  F  Q  A  E  L  W  I  K  E  L  T  S  V     348
1201  tatgattctcgagcacgagaaagattgcgccagattgaagaacagaaggcattggcctta
      Y  D  S  R  A  R  E  R  L  R  Q  I  E  E  Q  K  A  L  A  L     368
1261  cagcttcaaaaccagagattgcaggagcgggaacattcagtacatgattcagtagaacta
      Q  L  Q  N  Q  R  L  Q  E  R  E  H  S  V  H  D  S  V  E  L     388
1321  catcttcgtgtacctcttgaaaaggagattcctgttactgttgtccaagaaacacaaaaa
      H  L  R  V  P  L  E  K  E  I  P  V  T  V  V  Q  E  T  Q  K     408
1381  aaaggtcataaattaactgatagtgaagatgaatttcctgaaattacagagggaaatggag
      K  G  H  K  L  T  D  S  E  D  E  F  P  E  I  T  E  E  M  E     428
1441  aaagaaataaagaatgtatttcgtaatgggaatcaggatgaagttctcagtgaagcattt
      K  E  I  K  N  V  F  R  N  G  N  Q  D  E  V  L  S  E  A  F     448
1501  cgcctgaccattacacgcaaagatattcaaactctaaaccatctgaattggctcaatgat
      R  L  T  I  T  R  K  D  I  Q  T  L  N  H  L  N  W  L  N  D     468
1561  gagatcatcaatttctacatgaatatgctgatggagcgaagtaaagagaagggcttgcca
      E  I  I  N  F  Y  M  N  M  L  M  E  R  S  K  E  K  G  L  P     488
1621  agtgtgcatgcatttaataccttttcttcactaaattaaaaacggctggttatcaggca
      S  V  H  A  F  N  T  F  F  F  T  K  L  K  T  A  G  Y  Q  A     508
1681  gtgaaacgttggacaaagaaagtagatgtattttctgttgacattcttttggtgcccatt
      V  K  R  W  T  K  K  V  D  V  F  S  V  D  I  L  L  V  P  I     528
1741  cacctgggagtacactggtgtctagctgttgtggactttagaaagaagaatattacctat
      H  L  G  V  H  W  C  L  A  V  V  D  F  R  K  K  N  I  T  Y     548
1801  tacgactccatgggtggggataaacaatgaagcctgcagaatacttcttgcaatacctaaag
      Y  D  S  M  G  G  I  N  N  E  A  C  R  I  L  L  Q  Y  L  K     568
1861  caagaaagcattgacaagaaaaggaaagagtttgacaccaatggctggcagcttttcagc
      Q  E  S  I  D  K  K  R  K  E  F  D  T  N  G  W  Q  L  F  S     588
1921  aagaaaagccagattcctcagcagatgaatggaagtgactgtgggatgtttgcctgcaaa
      K  K  S  Q  I  P  Q  Q  M  N  G  S  D  C  G  M  F  A  C  K     608
1981  tatgctgactgtattaccaaagacagaccaatcaacttcacacagcaacacatgccatac
      Y  A  D  C  I  T  K  D  R  P  I  N  F  T  Q  Q  H  M  P  Y     628
2041  ttccggaagcggatggtctgggagatcctccaccgaaaactcttgtgaagactgtctcac
      F  R  K  R  M  V  W  E  I  L  H  R  K  L  L  *               643
2101  ttagcagaccttgaccatgtgggggaccagctctttgttgtctacagccagagaccttgg
2161  aaacagctgctcccagccctctgctgttgtaacacccttgatcctggaccaggccctggc
2221  gagatgcattcacaagcacatctgcctttcctttttgtatctcagatactattttgcaaa
2281  gaaactttggtgctgtgaaaggggtgagggacatccctaagctgaagagagagactgctt
2341  ttcacttcttcagttctgccatcttgttttcaaagggctccagcctcactcagtccctaa
```

2401 ttatgggactgagaaaagcttggaaagaatcttggtttcatataaattcttgttgctagg
2461 ccttactaagaagtaggaaagggcatgggcaaaaggtagggataaaaaccac

FIG. 2 CONTINUED

```
HsUlp1   MAEDGVRGSPPVPSGPPMEPEGLAWTPKSPLDPDSGLESCTLPNGFGGCSGPEGERSLAP    60
Ulp1              MSVEVCKHENTLQYHKKNPYSPLFSEISTYRCYPRVLNNPS-ESR        44
SENP1            MDDIADRKRMEAGEVELVNHNSVFKTHLL-EQTGFPEDQLSESDQQILSS     49

HsUlp1   PDASILISNVCSIGDHVAQELFQGSDLGMAEEAERPGEKE-SC----------------   102
Ulp1     RSASFSGIYKKRINTSRFNYLNDRRVLSMEESMKDGSDRASKAGFIGGIRETLWNSGKYL  104
SENP1    RQGHLDRSFTCSIRSAAYNPSYYSDNPSSDSFLGSGDLRTFGQSANGQWSNSTPSSSSSL  109

HsUlp1   ------------------------------------------------------------  102
Ulp1     WHTFVKNEPRNFD-----GSEVEASGNSDVESRSSGSRSS----DVEYGL-----RENYS  150
SENP1    QKSRNSRSLYETRKTSSGLSNSFACKSNHHCHVSAYEKSFPIKPVESPSWSGSCRRSLL   169

HsUlp1   ------------------------------------------------------------  102
Ulp1     SDTRKHKFDTSIWALPNKRRRIESE--------GVGTPSTSEISSLASQKSNCLSDNSIT  202
SENP1    SPKKTQRRHVSTAEETVQEEEREIYRQLLQMVTGKQFTIAKPTTHFPLHLSRCLSSSKNT  229

HsUlp1   ------------------------------------------------------------  102
Ulp1     FSRDPE-GWNKWKTSALGSNSENNISDQKNSYDRRQYGTAFIRKK---KVAKQNINNTKL  258
SENP1    LKDSLFKNGNSCASQILGSDTSSSGSASILTNQEQLSHSVYSLSSYTPDVAFGSKDSGTL  289

HsUlp1   ------------------------------------------------------------  102
Ulp1     VSRAQSEEVTYLRQIFNGEYKVPKILKEERERQLKEMDMDKEKDTGLKKSIIDLTEK-IK  317
SENP1    HHPHHHHSVPH-----QPDNLAASNTQSEGSDSVILLKV-KDSQTPTPSSTFFQAELWIK  343

HsUlp1   ------------------------------HSPLREEHVTCVQSILDEFLQTYG       126
Ulp1     TIL-IENNKNRLQTRNENDDDLVFVKEKKISSLEKHKDYLNQKLKFDRSILEFEKDFKR   376
SENP1    ELTSVYDSRAREREQIEEQKALALQLQNQRLQEEHSVHDSVELHL-RVPLEKEI----   398

HsUlp1   SLIPESTDEVV-EKLEDIFQQEFSTPSRKGLVLQLIQSYQRMPGNAMVRGFRVAYKEHVL  185
Ulp1     YNEILNERKKIQEDLKKKKEQLAKKKLVPELNEKDDDQVQKALASRENTQ-LMNRDNIEI  435
SENP1    ------PVTVVQETQKKGHKLTDSEDEFPEITEEMEKEIKNVFRNGNQDEVLSEAFRLTI  452

HsUlp1   GMDDLGTLYGQNWLNDQVMNMEGDLVEDTVPEK----VEFENSFFYDKLRTKGYLGVKRV  241
Ulp1     TVFDFKTLAPRRWLNDIIIEFEMKYI-----EKSTPNTVAFNSFFYTLLSERGYQGVRRW  490
SENP1    TRKDIQTLNHINVLNDEIINFYMNMLMERSKEKGLPSVHAFNTFFFTKLKTAGYQAVKRW  512

HsUlp1   TK--NVDIFNKELLLIPIHLEV-HWSLISVDVERRTITYFDSQRTLNRRCPKHIAKWLQA  298
Ulp1     MKRKKTQEDKLDKIFTPINLNQSEMALGIIELKKKTIGYVDSLSNGPNAMSFAILTDLQK  550
SENP1    TK--KVDVESVDILLVPIHLGV-HWCLAVVDFRKKNITYYDSMGGINNEACRILLQYLKQ  569

Ulp1     EAV-KKDRLDFHQGIKGYFK-MNVARQNNLSDCGAEVLQECKHLALSQPFSETQQDMPKL  356
Ulp1     YVMEESKH---TIGEDFDLIHLDCPQQPNGYDCCGIYVCNNTLYGSADAPLDFDYKEAIRM  607
SENP1    ESTDKKRKEFDENGIQLFSKKSQIPQQMNGSDCGMHACKYADCITKDRPINFTQQHMPYF  629

HsUlp1   ARQEYKELCECKETV                                               371
Ulp1     RRFIAHLILTDAEK                                               621
SENP1    RKRMVWEILHRKLL                                               643
```

FIG. 3

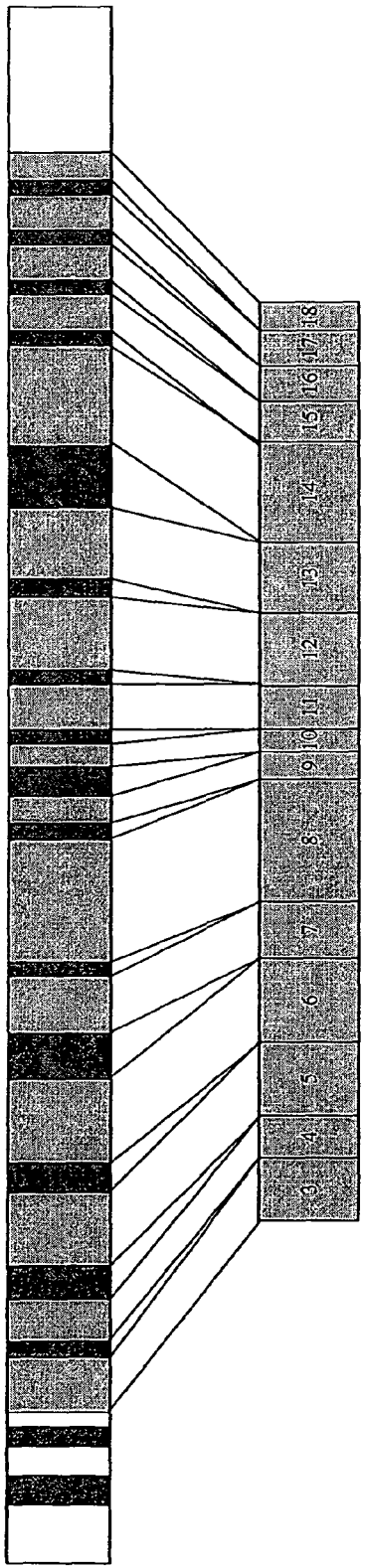

| EXON No. | Length (bp) | 5'Splice donor | Intron length(kb) | 3'Splice acceptor |
|---|---|---|---|---|
| 1 | 112 | GGTTCG GTGAGT | 4.4 | TTATAG GACTTT |
| 2 | 47 | AAATGG GTAAGA | 3.4 | CCCCAG ATGATA |
| 3 | 132 | CAGCAG GTTAGG | 1.5 | GTTTAG ATTTTA |
| 4 | 85 | ACTCAG GTATGA | 7.3 | TTTTAG ATAATC |
| 5 | 160 | CTCAAG GTTCGT | 5.0 | TTTTAG TGGATT |
| 6 | 172 | GAAGAG GTAAGG | 8.7 | TTATAG ACAGTT |
| 7 | 104 | ACACCT GTGAGT | 0.08 | TGCTAG GTCTCG |
| 8 | 284 | CTGAAG GTAAAC | 2.6 | TCTTAG GATCAG |
| 9 | 55 | TCCCAG GTAAAC | 4.7 | CCATAG TTCTAC |
| 10 | 39 | AGAATT GTAAGT | 1.2 | TTCTAG AACTAG |
| 11 | 85 | AACCAG GTAAAA | 0.37 | TTTCAG AGATTG |
| 12 | 156 | ACAGAG GTAAGT | 1.2 | CTCAAG GAAATG |
| 13 | 132 | GATGAG GTAATG | 14.4 | CCACAG ATCATC |
| 14 | 204 | AGCTGT GTAAGT | 0.84 | TCTCAG GTGTGT |
| 15 | 80 | ACTCTT GTAAGT | 0.94 | CTTTAG GCAATA |
| 16 | 85 | AGCCAG GTACCT | 0.53 | CAGGAG ATTCCT |
| 17 | 93 | ACACAG GTGAGC | 0.97 | CTACAG CAACAC |
| 18 | 487 | | | |

```
                    *
H_SENP1    PIHLGVHW-------------------------------------------------------
H_SENP2    PIHRKVHW-------------------------------------------------------
H_SENP3    PIHLEVHW-------------------------------------------------------
H_SENP4    PIHLEVHW-------------------------------------------------------
H_SENP5    PIHLEVHW-------------------------------------------------------
H_SENP6    PLNEAAHWFLAVVCFPGLEKPKYEPNPHYHENAVIQKCSTVEDSCISSSASEMESCSQNSSAKPVIKKML
H_SENP7    PVNESSHWYLAVICFPWLEEAVYEDFP--------Q---TV------SQQSQAQQSQN----------

H_SENP1    -----------------------------------------------------------
H_SENP2    -----------------------------------------------------------
H_SENP3    -----------------------------------------------------------
H_SENP4    -----------------------------------------------------------
H_SENP5    -----------------------------------------------------------
H_SENP6    NKKHCIAVIDSNPGQEESDPRYKRNICSVKYSVKKINHTASENEEFNKGESTSQKVADRTKSENGLQNES
H_SENP7    -----------------------------------------------------------

H_SENP1    ----------------------------------------------------------CLAVVDF
H_SENP2    ----------------------------------------------------------SLVVIDL
H_SENP3    ----------------------------------------------------------SLISVDV
H_SENP4    ----------------------------------------------------------SIISVDV
H_SENP5    ----------------------------------------------------------SLITVTL
H_SENP6    LSSTHHTDGLSKIRLNYSDESPEAGKMLEDELVDFSEDQDNQDDSSDDGFLADDNCSSEIGQWHLKPTIC
H_SENP7    -----------------------------DNKTIDNDLRTTSTLSLSAEDSQSTE-SNMSVPKKMC

*                                             *    *
H_SENP1    RKKNITYYDSMGGINNEAC-RILLQYLKQESIDKKRKEFDTNGWQLFSKKSQ-IPQQMNGSDCGMFACKY
H_SENP2    RKKCLKYLDSMGQKGHRIC-EILLQYLQDESKTKRNSDLNLLEWTHHSMKPHEIPQQLNGSDCGMFTCKY
H_SENP3    RRRTITYFDSQRTLNRR-CPKHIAKYLQAEAVKKDRLDF-HQGWKGYFKMN--VARQNNDSDCGAFVLQY
H_SENP4    RRRTITYYDSQRTVNRR-CPKHIAKYLQAEAVKKVRLDF-HQGWKGYFQMN--VARQNNDSGCGAFVLQY
H_SENP5    SNRIISFYDSQGIHFKF-CVENIRKYLLTEAREKNRPEF-LQGWQTAVTKC--IPQQKNDSDCGVFVLQY
H_SENP6    KQPCILLMDSLRGPSRSNVVKILREYLEVEWEVKKGSKRSFSKDVMKGSNPK-VPQQNNFSDCGVYVLQY
H_SENP7    KRPCILILDSLKAASVQNTVQNLREYLEVEWEVKLKTHRQFSKTNMVDLCPK-VPKQDNSSDCGVYLLQY
```

FIG. 7

COMPOSITION AND METHODS RELATING TO SENP1—A SENTRIN-SPECIFIC PROTEASE

This is a continuation of application Ser. No. 09/628,966, filed Jul. 31, 2000, which issued on Jul. 22, 2003 as U.S. Pat. No. 6,596,527. This application claims priority to U.S. provisional patent application 60/146,774, filed on Jul. 31, 1999, which is specifically incorporated by reference in its entirety herein without disclaimer.

This invention was made with government support under grant number HL-45851 awarded by the National Institutes of Health. The government has certain rights in the invention.

BACKGROUND OF THE INVENTION

1. Field of the Invention

The present invention relates generally to the field of molecular biology. More particularly, it concerns the elucidation and uses of de-sentrinase ("SENP1").

2. Description of Related Art

Sentrinization, a protein modification pathway present in all eukaryotic cells, is essential for cellular viability. The inventors have elucidated sentrin and the enzymatic mechanism required in the transfer of sentrin to its substrates (Okura et al., 1996; Kamitani et al., 1997a, b; Kamitani et al., 1998a; Kamitani et al., 1998b; Kamitani et al., 1998c; Gong et al., 1997; Gong et al., 1999). As shown in FIG. 1, sentrin is transferred through a unique. E1 complex (Aos1/Uba2) and E2 enzyme (Ubc9) to covalently modify a limited subset of cellular proteins (Gong et al., 1997; Gong et al., 1999).

Sentrin-1 (also called SUMO-1) is a protein that can covalently modify specific proteins in a manner analogous to ubiquitination (Okura et al., 1996; Kamitani et al., 1997a; Kamitani et al., 1997b; Matunis et al., 1996; Mahajan et al., 1997; Boddy et al., 1996; Hershko et al., 1998). In mammalian cells, there are three known sentrin family proteins that are expressed in all tissues and appear to have overlapping function (Kamitani et al., 1997a; Kamitani et al., 1997b; Kamitani et al., 1998a; Kamitani et al., 1998b).

It is now clear that the sentrinization pathway utilizes a unique activating-enzyme complex (Uba2/Aos1) and conjugation enzyme (Ubc9), to catalyze the modification of a subset of mammalian proteins, such as PML, Sp100, RanGAP1, RanBP2, IκBα, Cdc3, and cytomegalovirus IE1. (Matunis et al., 1996; Mahajan et al., 1997; Kamitani et al., 1998b; Kamitani et al., 1998c; Gong et al., 1997; Gong et al., 1999; Desterro et al., 1998; Muller et al., 1998; Sternsdorf et al., 1997; Saitoh et al., 1998). Other sentrinized proteins include Dorsal, GLUT1, GLUT4, HIPK2, p53, topoisomerase I and II, Werner syndrome gene product, MDM2, and bovine papilloma virus E1 (Yeh et al., 2000; Mao et al., 2000a; Mao et al., 2000b; Buschmann et al., 2000; Ramgasamy et al., 2000). Demonstration of sentrin modification in early studies was complicated by the presence of enzymes that cleaved the isopeptide linkage between sentrin and various target proteins in the cell lysate (Kamitani et al., 1997a; Kamitani et al., 1997b; Matunis et al., 1996). Thus, in analogy to the ubiquitin pathway (Wilkinson, 1997), enzyme(s) capable of removing sentrin from sentrinized proteins must also exist.

A *Saccharomyces cerevisiae* enzyme, Ulp1, was recently been shown to have de-conjugating activity for Smt-3 (yeast homologue of sentrin)-conjugated proteins and is required for cell cycle progression. Ulp1 was reported by Li et al., who showed that Ulp1 can remove Smt-3, the yeast homologue of sentrin-1, from its conjugates (Li and Hochstrasser, 1999). Ubp1 also cleaves sentrin-1/SUMO-1, but not ubiquitin, from modified proteins in vitro. Ulp1 is not related to any known de-ubiquitinating enzyme. Li et al. also cited a partial EST sequence, tentatively called HsUlp1, which is homologous to yeast Ulp1.

SUMMARY OF THE INVENTION

The inventors' invention embodies the first description of a human de-sentrinase, SENP1. The inventors have cloned a novel protease, called SENP1, which is active against sentrin, but not ubiquitin or NEDD8-modified proteins in vivo. The inventors also elucidate the genomic organization of the SENP1 gene and show that SENP1 differentially regulates sentrin-modified proteins in vivo.

The invention relates generally to compositions of and methods for obtaining de-sentrinase (SENP1) polypeptides. The invention relates as well to polynucleotides encoding SENP1 polypeptides, the recombinant vectors carrying those sequences, the recombinant host cells including either the sequences or vectors, and recombinant de-sentrinase polypeptides. By way of example, the invention discloses the cloning and functional expression of the SENP1 polypeptides. The invention includes as well, methods for using the isolated, recombinant SENP1 polypeptides in assays designed to select and improve substances capable of interacting with SENP1 polypeptides for use in diagnostic, drug design and therapeutic applications. Such substances may specifically bind to SENP1. Candidate substances that affect the activity of SENP1, such as by altering its ability to remove sentrin from sentrinized proteins may be considered modulators of SENP1.

Ulp1 is distantly related to SENP1 via sequence analysis. However, it cannot be identified through BLAST search using SENP1 polypeptide sequence. The inventors cloned the complete coding sequence of HsUlp1 and found that it did not possess protease activity against sentrin-1 conjugates. Therefore, there appears to be no functional relationship between Ulp1 and SENP1.

In some embodiments, the invention relates to isolated and purified polynucleotides or nucleic acid sequences. These nucleic acid sequences may be sequences of almost any length of nucleotides from SEQ ID NO:1, SEQ ID NO:7, or SEQ ID NO:9, or variants thereof. Such nucleic acid sequences may, be identical or complementary to all or part of SEQ ID NO:1, SEQ ID NO:7, or SEQ ID NO:9. For example, these nucleic acids may encode probes, primers, truncated coding sequences, full length coding sequences, and expression constructs. These nucleic acid sequences may be comprised within genetically engineered constructs, vectors, plasmids, eukaryotic or prokaryotic host cells, or any other suitable. These nucleic acids may be DNA or RNA from a natural or synthetic source. These nucleic acids may comprise modified bases. In certain preferred embodiments, these nucleic acids will encode a peptide sequence comprising having all or a portion of the amino acid sequence of SENP1.

In other aspects, the invention relates to polypeptides comprising all or part of the amino acid sequence of SEQ ID NO:2, SEQ ID NO:8, or SEQ ID NO:10, including truncated, modified, mutated, or natural or engineered variants thereof. Methods for producing such polypeptides are described elsewhere in the application.

In some embodiments, the invention relates to the methods for preparing polypeptides comprising: transfecting a cell with a polynucleotide sufficient to produce a transformed host cell; and maintaining the transformed host cell under biological conditions sufficient for expression of the polypeptide. The polynucleotides used in this method and polypeptides obtained from this method may be any of the polynucleotides described above. In particular this method may be used to produce to polypeptides comprising all or part of the amino acid sequence of SEQ ID NO:2, SEQ ID NO:8, and SEQ ID NO:10, including truncated, modified, mutated, or natural or engineered variants thereof. These methods may further comprise steps of purifying the obtained polynucleotides by any number of known methods described below.

These methods may also comprise steps of assaying the expressed polypeptides for activity or using the expressed polypeptides to assay any of a number of candidate substances for activity, as described elsewhere in this application. When such activity assays are done, they may be done in with purified polypeptide, polypeptides contained in a crude cell extract, or polypeptides contained in more or less intact host cells expressing the polypeptides. In more specific embodiments, the invention contemplates methods for using isolated, recombinant SENP1 polypeptides in assays designed to select and improve substances capable of interacting with SENP1 polypeptides for use in diagnostic, drug design and therapeutic applications such as anti-proliferative, anti-Herpes simplex 1, anti-CMV therapy, and other therapies as are described elsewhere in the specification and will be apparent to those of skill in the art in view of this specification.

Consistent with long-standing patent law, the words "a" and "an" denote "one or more," when used in the text or claims of this specification conjunction with the word "comprising" or where the context of the usage suggests that, from either a grammatical or scientific standpoint, these words should so denote.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. cDNA and amino acid sequences of SENP1.

Shown in this figure are the cDNA sequence (SEQ ID NO: 1) and putative amino acid sequence (SEQ ID NO:2) of human SENP1.

FIG. 3. Sequence alignment of SENP1, Ulp1, and HsUlp1

Identical amino acids are shaded block. Residues of the putative catalytic triad (histidine, aspartate and cysteine) and an invariant glutamine residue are marked by dots. Accession number for SENP1, Ulp1, and HsUlp1 are AF149770, AAB68167, and AF151697, respectively.

FIG. 4A and FIG. 4B. Genomic organization of SENP1

FIG. 4A shows that SENP1 is located in 12q13.1 and spans about 61 kb. SENP1 gene is composed of 18 distinct exons.

FIG. 4B shows the exon and intron organization of the human SENP1 gene. The 5' acceptors GT and the 3' donor AG are underlined. The exonic sequences are printed in bold.

Figure 5A:
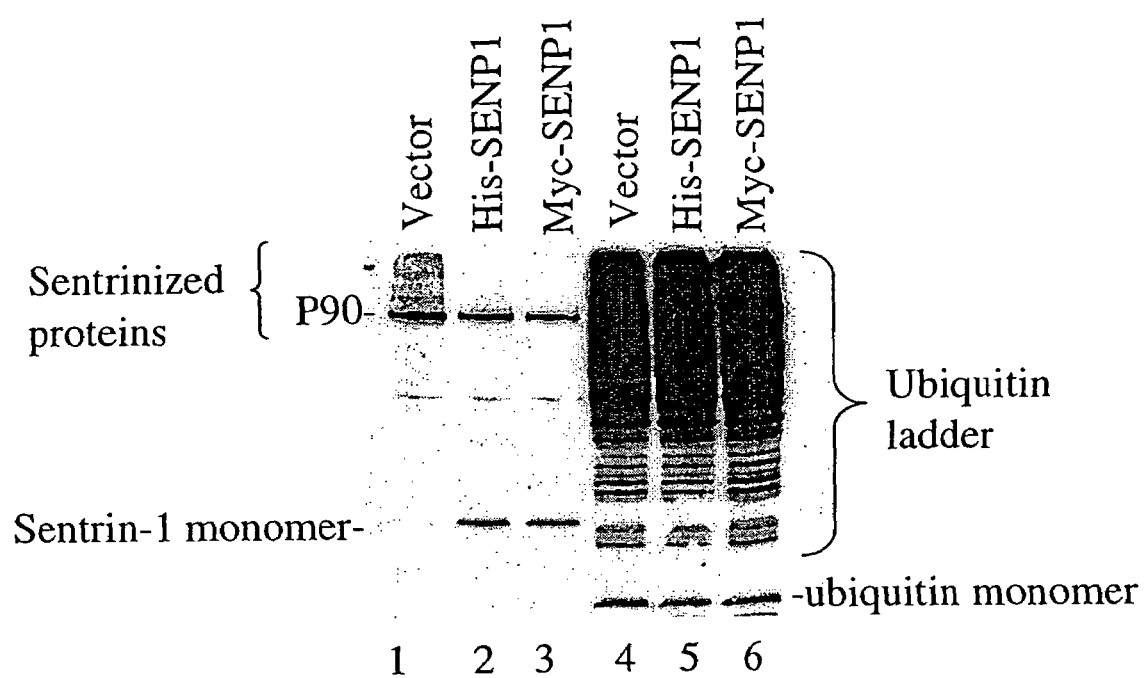
Figure 5B:
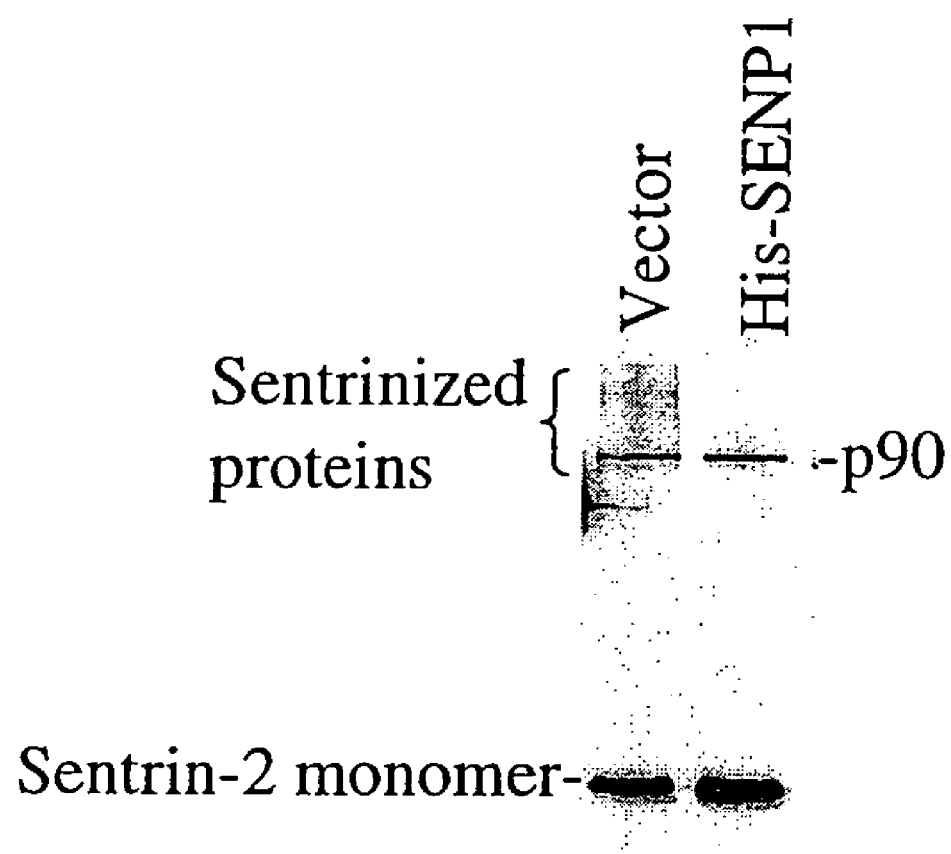
Figure 5C:
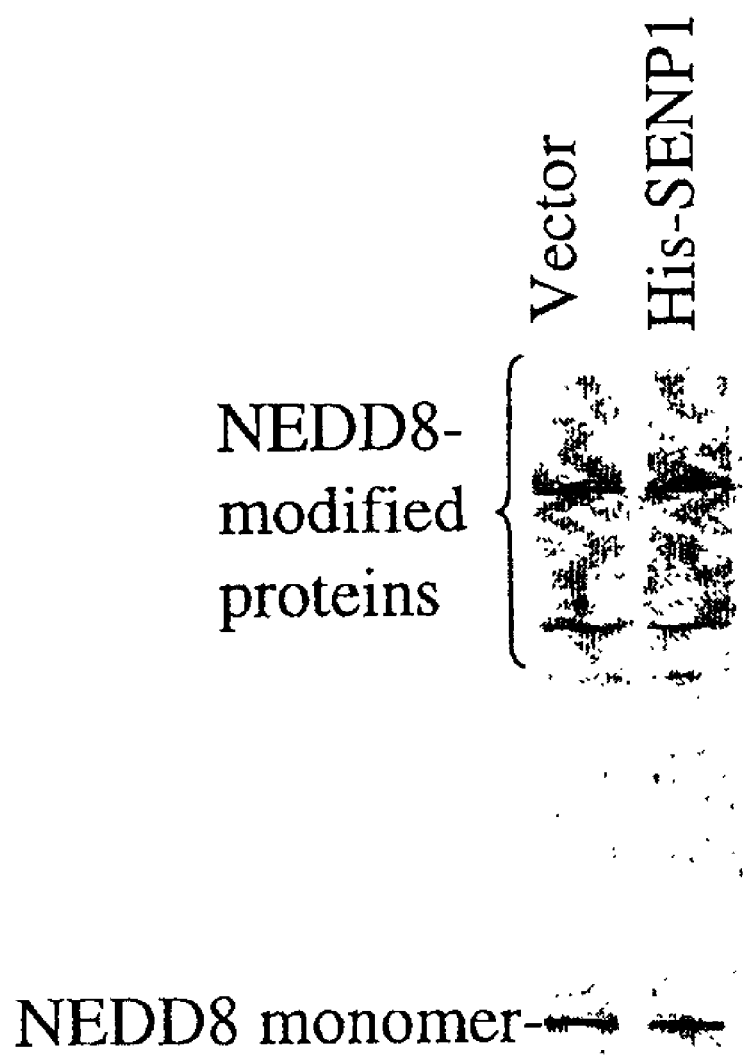

FIG. 5A, FIG. 5B, and FIG. 5C. SENP1 is a sentrin-specific protease.

In FIG. 5A, HA-sentrin-1 was co-expressed in COS cells with vector control (lane 1), His-SENP1 (lane 2), and Myc-SENP1 (lane 3). HA-ubiquitin was co-expressed in COS cells with vector control (lane 4), His-SENP1 (lane 5), and Myc-SENP1 (lane 6). Total cell lysates were analyzed by immunoblotting with an anti-HA monoclonal antibody. Sentrinized proteins, p90, sentrin-1 monomer, ubiquitin ladder, and ubiquitin monomer are indicated.

In FIG. 5B, HA-sentrin-2 was co-expressed in COS cells with vector control (lane 1) or His-SENP1 (lanes 2). Total cell lysates were analyzed by immunoblotting with an anti-HA monoclonal antibody. Sentrinized proteins, p90, and sentrin-2 monomer are indicated.

In FIG. 5C, HA-NEDD8 was co-expressed in COS cells with vector control (lane 1) or His-SENP1 (lanes 2). Total cell lysates were analyzed by immunoblotting with an anti-HA monoclonal antibody. NEDD8-modified proteins and NEDD8 monomer are indicated.

Figure 6:
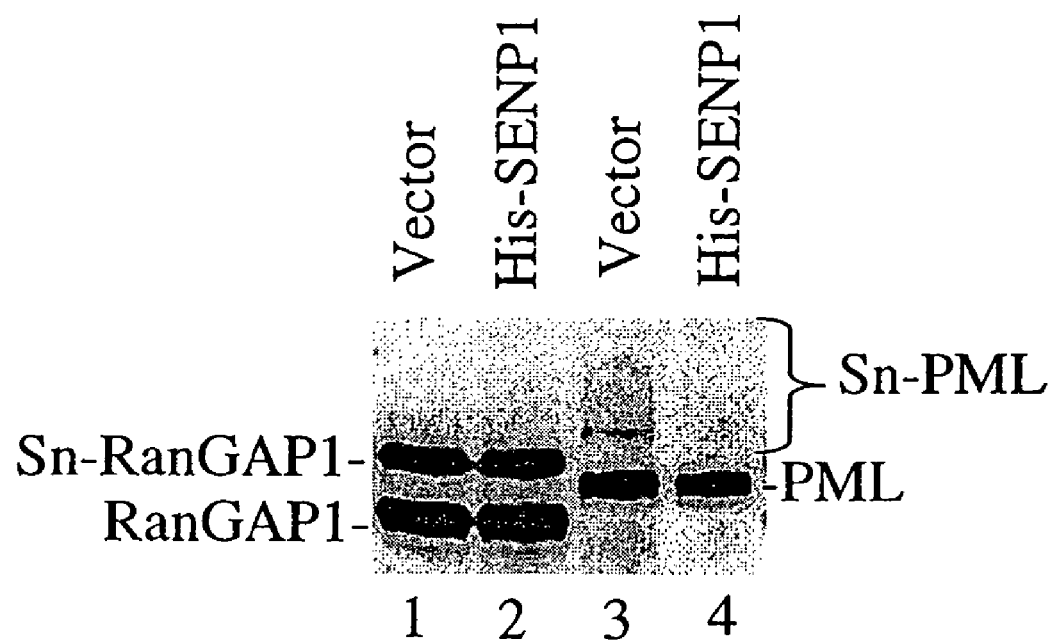

FIG. 6. SENP1 processes sentrinized PML, but not sentrinized RanGAP1

HA-PML was co-expressed in COS cells with vector control (lane 1) or His-SENP1 (lane 2). HA-RanGAP1 was co-expressed in COS cells with vector control (lane 3) or His-SENP1 (lane 4). Total cell lysates were analyzed by immunoblotting with an anti-HA monoclonal antibody. Sn-RanGAP1, sentrinized RanGAP1; Sn-PML, sentrinized PML.

FIG. 7. Conserved regions of human Sentrin-specific proteases.

DESCRIPTION OF ILLUSTRATIVE EMBODIMENTS

The inventors cloned a novel sentrin-specific protease, SENP1, which has no homology to the known de-ubiquitinating enzyme or ubiquitin C-terminal hydrolases. A COS cell expression system was used to demonstrate the activity of SENP1 in vivo. When HA-tagged sentrin-1 was co-expressed with His-tagged SENP1, the higher molecular weight sentrin-1 conjugates were completely removed. However, the 90 kDa band, which most likely represents sentrinized RanGAP1, remained intact. The disappearance of the high molecular weight sentrin-1 conjugates also coincided with the generation of free sentrin-1 monomers. The activity of SENP1 is restricted to all sentrin family members because it has no activity against ubiquitin- or NEDD8-modified proteins. The inability of SENP1 to decrease the 90 kDa band suggests that SENP1 cannot remove sentrin from all sentrinized proteins. The inventors further showed that sentrinized PML, but not RanGAP1, is selectively affected by SENP1. Taken together, SENP1 provides a unique tool to study the role of sentrinization in the biological function of PML, a tumor suppressor protein implicated in the pathogenesis of acute promyelocytic leukemia.

A. NUCLEIC ACIDS

As described in the Examples which follow, the present invention discloses the SENP1.

In one embodiment of the present invention, the nucleic acid sequences disclosed herein find utility as hybridization probes or amplification primers. In certain embodiments, these probes and primers consist of oligonucleotide fragments. Such fragments should be of sufficient length to provide specific hybridization to an RNA or DNA sample extracted from tissue. The sequences typically will be 10-20 nucleotides, but may be longer. Longer sequences, e.g., 40, 50, 100, 500 and even up to full length, are preferred for certain embodiments.

Nucleic acid molecules having contiguous stretches of for example about 10, 15, 17, 20, 25, 30, 35, 40, 45, 50, 55, 60, 70, 75, 80, 85, 90, 95, 100, 125, 150, 175, 200, 250, 300, 350, 400, 500, 600, 700, 800, 900, 1000, 1250, 1500, 1750, 2000, 2100, up to full length from SEQ ID NO:1, SEQ ID NO:7, or SEQ ID NO:9, fragments thereof, mRNAs and cDNAs encoding SEQ ID NO:1, SEQ ID NO:7, or SEQ ID NO:9, and mutants of each are contemplated. It is also contemplated that nucleic acid molecules may be at least the lengths recited above. Molecules that are complementary to the above mentioned sequences and that bind to these sequences under high stringency conditions also are contemplated. These probes will be useful in a variety of hybridization embodiments, such as Southern and northern blotting. In some cases, it is contemplated that probes may be used that hybridize to multiple target sequences. In certain embodiments, it is contemplated that multiple probes may be used for hybridization to a single sample. It is contemplated that any composition or method described herein with respect to SEQ ID NO:1 may be implemented with respect to SEQ ID NO:7 or SEQ ID NO:9.

Various probes and primers can be designed around the disclosed nucleotide sequences. Primers may be of any length but, typically, are 10-20 bases in length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The value of n in the algorithm above for the nucleic acid sequence is n=49,136 for the SENP1 gene. The value of n for a cDNA encoding SENP1 may be calculated by adding up the number of nucleic acids in the exons that are spliced to form the mRNA from which SENP1 is expressed.

The use of a hybridization probe of between 17 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It will be understood that this invention is not limited to the particular probes disclosed herein and particularly is intended to encompass at least nucleic acid sequences that are hybridizable to the disclosed sequences or are functional analogs of these sequences.

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

In an alternative embodiment, the SENP1 encoding nucleic acids employed may actually encode antisense constructs that hybridize, under intracellular conditions, to an SENP1 or other encoding nucleic acid. The term "antisense construct" is intended to refer to nucleic acids, preferably oligonucleotides, that are complementary to the base sequences of a target DNA or RNA. Antisense oligonucleotides, when introduced into a target cell, specifically bind to their target nucleic acid and interfere with transcription, RNA processing, transport, translation and/or stability.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" means nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

While all or part of the SENP1 gene sequence may be employed in the context of antisense construction, short oligonucleotides are easier to make and increase in vivo accessibility. However, both binding affinity and sequence specificity of an antisense oligonucleotide to its complementary target increases with increasing length. It is contemplated that antisense oligonucleotides of 8, 9, 10, 11, 12, 13, 14, 15, 16, 17, 18, 19, 20, 25, 30, 35, 40, 45, 50, 60, 70, 80, 90, 100 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 1 and 2 list several elements/promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 2

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| α-Globin |
| β-Globin |
| c-fos |
| c-HA-ras |
| Insulin |
| Neural Cell Adhesion Molecule (NCAM) |
| $\alpha_1$-Anti-trypsin |
| H2B (TH2B) Histone |
| Mouse or Type I Collagen |
| Glucose-Regulated Proteins (GRP94 and GRP78) |

TABLE 2-continued

| PROMOTER |
| --- |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |

Use of the baculovirus system will involve high level expression from the powerful polyhedrin promoter.

One will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

In various embodiments of the invention, the expression construct may comprise a virus or engineered construct derived from a viral genome. The ability of certain viruses to enter cells via receptor-mediated endocytosis and to integrate into the host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of expressing proteins of interest or (ii) to transform cells in vitro or in vivo to provide therapeutic polypeptides in a gene therapy scenario.

In some embodiments, the vector is HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings.

B. ENCODED PROTEINS

Once the entire coding sequence of a particular gene has been determined, the gene can be inserted into an appropriate expression system. In this case, the inventors have identified the SENP1 gene. The gene can be expressed in any number of different recombinant DNA expression systems to generate large amounts of the polypeptide product, which can then be purified and used to vaccinate animals to generate antisera with which further studies may be conducted. For example, the gene may be expressed to obtain an SENP1 polypeptide as set forth in SEQ ID NO:2. It is contemplated that any composition or method discussed with respect to SEQ ID NO:2, may be implemented with respect to SEQ ID NO:8 and/or SEQ ID NO:10. Alternatively, any embodiment described herein with respect to SENP1, may be applied to SENP2 and/or SENP3.

Examples of expression systems known to the skilled practitioner in the art include bacteria such as *E. coli*, yeast such as *Saccharomyces cerevisia* and *Pichia pastoris*, baculovirus, and mammalian expression systems such as in COS or CHO cells. In one embodiment, polypeptides are expressed in *E. coli* and in baculovirus expression systems. A complete gene can be expressed or, alternatively, fragments of the gene encoding portions of polypeptide can be produced.

In one embodiment, the gene sequence encoding the polypeptide is analyzed to detect putative transmembrane sequences. Such sequences are typically very hydrophobic and are readily detected by the use of standard sequence analysis software, such as DNA Star (DNA Star, Madison, Wis.). The presence of transmembrane sequences is often deleterious when a recombinant protein is synthesized in many expression systems, especially *E. coli*, as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Therefore, antibodies to these sequences will not prove useful for in vivo or in situ studies. Deletion of transmembrane-encoding sequences from the genes used for expression can be achieved by standard techniques. For example, fortuitously-placed restriction enzyme sites can be used to excise the desired gene fragment, or PCR-type amplification can be used to amplify only the desired part of the gene. The skilled practitioner will realize that such changes must be designed so as not to change the translational reading frame for downstream portions of the protein-encoding sequence.

In one embodiment, computer sequence analysis is used to determine the location of the predicted major antigenic determinant epitopes of the polypeptide. Software capable of carrying out this analysis is readily available commercially, for example DNA Star (DNA Star, Madison, Wis.). The software typically uses standard algorithms such as the Kyte/Doolittle or Hopp/Woods methods for locating hydrophilic sequences which are characteristically found on the surface of proteins and are, therefore, likely to act as antigenic determinants.

Once this analysis is made, polypeptides can be prepared that contain at least the essential features of the antigenic determinant and that can be employed in the generation of antisera against the polypeptide. Minigenes or gene fusions encoding these determinants can be constructed and inserted into expression vectors by standard methods, for example, using PCR methodology.

The gene or gene fragment encoding a polypeptide can be inserted into an expression vector by standard subcloning techniques. In one embodiment, an *E. coli* expression vector is used that produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (New England Biolabs, Beverley, Mass.), the FLAG system (IBI, New Haven, Conn.), and the 6×His system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6×His system add only short sequences, both of that are known to be poorly antigenic and which do not adversely affect folding of the polypeptide to its native conformation. Other fusion systems produce polypeptide where it is desirable to excise the fusion partner from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

Recombinant bacterial cells, for example *E. coli*, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

In another embodiment, the expression system used is one driven by the baculovirus polyhedron promoter. The gene encoding the polypeptide can be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See Summers et al, A MANUAL OF METHODS FOR BACULOVIRUS VECTORS AND INSECT CELL CULTURE PROCEDURES, Texas Agricultural Experimental Station.

As an alternative to recombinant polypeptides, synthetic peptides corresponding to the antigenic determinants can be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

In one embodiment, amino acid sequence variants of the polypeptide can be prepared. These may, for instance, be minor sequence variants of the polypeptide that arise due to natural variation within the population or they may be homologues found in other species. They also may be sequences that do not occur naturally but that are sufficiently similar that they function similarly and/or elicit an immune response that cross-reacts with natural forms of the polypeptide. Sequence variants can be prepared by standard methods of site-directed mutagenesis such as those described below in the following section.

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR™ can be used to prepare a range of cDNAs encoding peptides lacking successively longer fragments of the C-terminus of the protein. The immunoprotective activity of each of these peptides then identifies those fragments or domains of the polypeptide that are essential for this activity. Further experiments in which only a small number of amino acids are removed at each iteration then allows the location of the antigenic determinants of the polypeptide.

Another embodiment for the preparation of the polypeptides according to the invention is the use of peptide mimetics. Mimetics are peptide-containing molecules that mimic elements of protein secondary structure. See, for example, Johnson et al, "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within an polypeptide can be predicted by computer-based algorithms as discussed above. Once the component amino acids of the turn are determined, peptide mimetics can be constructed to achieve a similar spatial orientation of the essential elements of the amino acid side chains.

Modification and changes may be made in the structure of a gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by changing the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte &.Doolittle, 1982).

TABLE 4

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

C. SITE-SPECIFIC MUTAGENESIS

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

D. EXPRESSION AND PURIFICATION OF ENCODED PROTEINS

1. Expression of Proteins from Cloned cDNAs

The cDNA species specified in SEQ ID NO:1, SEQ ID NO:7, or SEQ ID NO:9 can be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

In certain embodiments, the present invention concerns novel compositions comprising at least one proteinaceous molecule, such as SENP1, SENP2, and SENP3. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein. Furthermore, these terms may be applied to fusion proteins as well.

In certain embodiments the size of the at least one proteinaceous molecule may comprise, but is not limited to, about or at least 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, 800, 850, 900, 950, 1000, 1100, 1200, 1300, 1400, 1500, 1750, 2000, 2250, 2500 or greater amino molecule residues, and any range derivable therein, particularly contiguous amino acid sequences of such lengths from SEQ ID NO:2, SEQ ID NO:8, or SEQ ID NO:10.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic DNA, and also include genes positioned adjacent to a promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* χ 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used (Stinchcomb et al., 1979; Kingsman et al., 1979; Tschemper et al., 1980). This plasmid contains the trp1 gene, which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autograph californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, WI38, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HinDIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk$^-$, hgprt$^-$ or aprt$^-$ cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan et al., 1981); neo, which confers resistance to the aminoglycoside G-418 (Colberre-Garapin et al., 1981); and hygro, which confers resistance to hygromycin.

It is contemplated that the isolated nucleic acids of the invention may be "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

2. Purification of Expressed Proteins

Further aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or β-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., Biochem. Biophys. Res. Comm., 76:425, 1977). It will therefore be appreciated that under differing electrophoresis conditions, the apparent molecular weights of purified or partially purified expression products may vary.

E. PREPARATION OF ANTIBODIES SPECIFIC FOR SENP1

Antibody Generation

For some embodiments, it will be desired to produce antibodies that bind with high specificity to the protein product(s) of an isolated nucleic acid encoding for SENP1. Such antibodies may be used in any of a variety of applications known to those of skill in the art, including but not limited to: immunodetection methods, immunoprecipitation methods, ELISA assays, protein purigication methods, etc.

Means for preparing and characterizing antibodies are well known in the art (See, e.g., Harlow and Lane, Antibodies: A Laboratory Manual, Cold Spring Harbor Laboratory, 1988, incorporated herein by reference).

Methods for generating polyclonal antibodies are well known in the art. Briefly, a polyclonal antibody is prepared by immunizing an animal with an antigenic composition and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or in some cases the animal can be used to generate monoclonal antibodies (MAbs). For production of rabbit polyclonal antibodies, the animal can-be bled through an ear vein or alternatively by cardiac puncture. The removed blood is allowed to coagulate and then centrifuged to separate serum components from whole cells and blood clots. The serum may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner that effectively stimulates antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas).

Any one of a number of myeloma cells may be used, as are known to those of skill in the art (Goding, 1986). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this low frequency does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and thus they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity, assays, plaque assays, dot immunobinding assays, and the like.

The selected hybridomas would then be serially diluted and cloned into individual antibody-producing cell lines, which can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals that are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or by expression of full-length gene or of gene fragments in *E. coli*.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^{3}H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, $^{75}Se$, $^{52}Eu$, and $^{99m}Tc$, are other useful labels that can be conjugated to antibodies. Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$ by ligand exchange process, for example, by reducing pertechnate with stannous solution, chelating the reduced technetium onto a Sephadex column and applying the antibody to this column or by direct labelling techniques, e.g., by incubating pertechnate, a reducing agent such as $SnCl_2$, a buffer solution such as sodium-potassium phthalate solution, and the antibody.

F. METHODS FOR SCREENING ACTIVE COMPOUNDS

The present invention also contemplates the use of SENP1 and active fragments, and nucleic acids coding therefor, in the screening of compounds for activity in either stimulating SENP1 activity, overcoming the lack of SENP1 activity or blocking the effect of a SENP1 molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound.

Compounds thus identified will be capable of promoting gene expression, and thus can be said to have up-regulating activity. Before human administration, such compounds would be rigorously tested using conventional animal models known to those of skill in the art.

As stated earlier, the present invention provides the complete sequence of the SENP1 gene.

Virtually any candidate substance may be analyzed by these methods, including compounds which may interact with SENP1, SENP1 binding protein(s), and substances such as enzymes, which may act by physically altering one of the structures present. Similarly, these methods may be employed with respect to SENP2 or SENP3, which may be substituted for SENP1 in any of the protocols, processes, or methods described below. Thus, if an altered version of SENP1 is discussed with any of the methods described herein, it is contemplated that a similar version of SENP2 or SENP3 may be used also. Of course, any compound isolated from natural sources such as plants, animals or even marine, forest, or soil samples, may be assayed, as may any synthetic chemical or recombinant protein. It is further envisioned that proteins that are possible substrates for SENP1 (subset of SENP1 binding proteins) may be used in screening assays with SENP1. For instance, a protein that is sentrinized may be used to characterize, quantitate, or assay for SENP1 activity. Alternatively, such proteins may be used in other aspects of the invention, such as to inhibit SENP1 activity, particularly if the protein were modified. Rational drug design, discussed herein, may be based on one or more of these substrate proteins. Examples of such proteins include PML, Sp100, RanGAP1, RanBP2, IκBα, Cdc3, cytomegalovirus IE1, Dorsal, GLUT1, GLUT4, HIPK2, p53, topoisomerase I and II, Werner syndrome gene product, MDM2, and bovine papilloma virus E1.

1. In Vitro Assays

In one embodiment, the invention is to be applied for the screening of compounds that bind, specifically or, non-specifically, to the SENP1 wild-type molecule, mutant or fragment thereof. The wild-type or mutant polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of SENP1 to a natural or artificial substrate or binding partner. Competitive binding assays can be performed in which one of the agents (SENP1, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with SENP1 and washed. Bound polypeptide is detected by various methods.

Purified SENP1 can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the SENP1 active region to a solid phase.

Various cell lines containing wild-type or natural or engineered mutations in SENP1 can be used to study various functional attributes of SENP1 and how a candidate compound affects these attributes. Methods for engineering mutations are described elsewhere in this document, as are naturally-occurring mutations in SENP1 that lead to, contribute to and/or otherwise cause disease states. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of SENP1, or related pathways, may be explored. This may involve assays such as those for protein expression, enzyme function, substrate utilization, phosphorylation states of various molecules, cAMP levels, mRNA expression (including differential display of whole cell or polyA RNA) and others.

2. In Vivo Assays

The present invention also encompasses the use of various animal models. Here, the identity seen between SENP1 and other SENP Is provides an excellent opportunity to examine the function of SENP1 in relation to other proteases in a whole animal system where it is normally expressed. By developing or isolating mutant cells lines that fail to express normal SENP1, one can generate models in mice that will be highly predictive of various disease states, including herpes simplex 1, cell proliferation, and acute promyelocytic leukemia in humans and other mammals.

Alternatively, one may increase the susceptibility of an animal to disease by providing agents known to be responsible for this susceptibility, i.e., providing a mutant SENP1. Finally, transgenic animals (discussed below) that lack a wild-type SENP1 may be utilized as models for disease development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection and regional administration via blood or lymph supply.

Determining the effectiveness of a compound in vivo may involve a variety of different criteria. Such criteria include, but are not limited to, survival, improvement of hyperglycemia, diminished need for hypoglycemic agents, diminished need for insulin requirements, increased insulin synthesis, improved protease activity, improvement in immune effector function and improved food intake.

3. Reporter Genes and Cell-Based Screening Assays

Cellular assays also are available for screening candidate substances to identify those capable of stimulating SENP1 activity and gene expression. In these assays, the increased expression of any natural or heterologous gene under the control of a functional SENP1 promoter may be employed as a measure of stimulatory activity, although the use of reporter genes is preferred.

A reporter gene is a gene that confers on its recombinant host cell a readily detectable phenotype that emerges only under specific conditions. In the present case, the reporter gene may be placed under the control of the same promoter as the SENP1 and will thus generally be repressed under conditions where the SENP1 is not being expressed and will generally be expressed in the conditions where SENP1 is being expressed.

Reporter genes are genes which encode a polypeptide not otherwise produced by the host cell which is detectable by analysis of the cell culture, e.g., by fluorometric, radioisotopic or spectrophotometric analysis of the cell culture. Exemplary enzymes include luciferases, transferases, esterases, phosphatases, proteases (tissue plasminogen activator or urokinase), and other enzymes capable of being detected by their physical presence or functional activity. A reporter gene often used is chloramphenicol acetyltransferase (CAT) which may be employed with a radiolabeled substrate, or luciferase, which is measured fluorometrically.

Another class of reporter genes which confer detectable characteristics on a host cell are those which encode polypeptides, generally enzymes, which render their transformants resistant against toxins, e.g., the neo gene which protects host cells against toxic levels of the antibiotic G418, and genes encoding dihydrofolate reductase, which confers resistance to methotrexate. Genes of this class are not generally preferred since the phenotype (resistance) does not provide a convenient or rapid quantitative output. Resistance to antibiotic or toxin requires days of culture to confirm, or complex assay procedures if other than a biological determination is to be-made.

Other genes of potential for use in screening assays are those capable of transforming hosts to express unique cell surface antigens, e.g., viral env proteins such as HIV gp120 or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstances the signal is modified in order to remove sequences that interdict secretion. For example, the herpes gD coat protein has been modified by site directed deletion of its transmembrane binding domain, thereby facilitating its secretion (EP 139,417A). This truncated form of the herpes gD protein is detectable in the culture medium by conventional immunoassays. Preferably, however, the products of the reporter gene are lodged in the intracellular or membrane compartments. Then they can be fixed to the culture container, e.g., microtiter wells, in which they are grown, followed by addition of a detectable signal generating substance such as a chromogenic substrate for reporter enzymes.

To create an appropriate vector or plasmid for use in such assays one would ligate the promoter, whether a hybrid or the native SENP1-1 promoter, to a DNA segment encoding the reporter gene by conventional methods. The SENP1-1 promoter sequences may be obtained by in vitro synthesis or recovered from genomic DNA and should be ligated upstream of the start codon of the reporter gene. The present invention provides the promoter region for human SENP1 gene. Any of these promoters may be particularly preferred in the present invention. An AT-rich TATA box region should also be employed and should be located between the SENP1 sequence and the reporter gene start codon. The region 3' to the coding sequence for the reporter gene will ideally contain a transcription termination and polyadenylation site. The promoter and reporter gene may be inserted into a replicable vector and transfected into a cloning host such as *E. coli*, the host cultured and the replicated vector recovered in order to prepare sufficient quantities of the construction for later transfection into a suitable eukaryotic host.

Host cells for use in the screening assays of the present invention will generally be mammalian cells, and are preferably cell lines which may be used in connection with transient transfection studies. Cell lines should be relatively easy to grow in large scale culture. Also, they should contain as little native background as possible considering the nature of the reporter polypeptide. Examples include the Hep G2, VERO, HeLa, human embryonic kidney (HEK)-293, CHO, W138, BHK, COS-7, and MDCK cell lines, with monkey CV-1 cells being particularly preferred.

In one embodiment, the screening assay typically is conducted by growing recombinant host cells in the presence and absence of candidate substances and determining the amount or the activity of the reporter gene. To assay for candidate substances capable of exerting their effects in the presence of SENP1 gene products, one would make serial molar proportions of such gene products that alter SENP1-mediated activity. One would ideally measure the reporter signal level after an incubation period that is sufficient to demonstrate mutant-mediated repression of signal expression in controls incubated solely with mutants. Cells containing varying proportions of candidate substances would then be evaluated for signal activation in comparison to the suppressed levels.

Candidates that demonstrate dose related enhancement of reporter gene transcription or expression are then selected for further evaluation as clinical therapeutic agents. The stimulation of activity may be observed in the absence of SENP1, in which case the candidate compound might be a positive stimulator of SENP1 expression. Alternatively, the candidate compound might only give a stimulation in the presence of a SENP1 protein having the G-allele, which would indicate that it functions to oppose the G-allele-mediated suppression of activity. Candidate compounds of either class might be useful therapeutic agents that would combat any number of types of diseases.

4. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for SENP1 or a fragment thereof This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a SENP1-specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved SENP1 activity or which act as stimulators, inhibitors, agonists, antagonists of SENP1 or molecules affected by SENP1 function. By virtue of the availability of cloned SENP1 sequences, sufficient amounts of SENP1 can be produced to perform crystallographic studies. In addition, knowledge of the polypeptide sequences permits computer employed predictions of structure-function relationships.

G. DETECTION AND QUANTITATION OF NUCLEIC ACID SPECIES

One embodiment of the instant invention comprises a method for identification of SENP1 mutants in a biological sample by amplifying and detecting nucleic acids corresponding to SENP1 mutants. The biological sample can be any tissue or fluid in which these mutants might be present. Various embodiments include bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, lymph fluid, ascites, serous fluid, pleural effusion, sputum, cerebrospinal fluid, lacrimal fluid, stool or urine.

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to SENP1 mutants are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a reference group of normal subjects or indeed patients with a given disease. In this way, it is possible to correlate the amount of SENP1 mutants detected with various clinical states.

1. Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

2. Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labelling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989); Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS: A GUIDE TO METHODS AND APPLICATIONS*, Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., 1989), incorporated herein by reference in its entirety.

3. RNase Protection Assay

Methods for genetic screening by identifying mutations associated with most genetic diseases such as those based on SENP1 mutations must be able to assess large regions of the genome. Once a relevant mutation has been identified in a given patient, other family members and affected individuals can be screened using methods which are targeted to that site. The ability to detect dispersed point mutations is critical for genetic counseling, diagnosis, and early clinical intervention as well as for research into the etiology of cancer and other genetic disorders. The ideal method for genetic screening would quickly, inexpensively, and accurately detect all types of widely dispersed mutations in genomic. DNA, cDNA, and RNA samples, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others (Cotton, 1989). The more common procedures currently in use include direct sequencing of target regions amplified by PCR™ and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations. U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as +.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A Other investigators have described the use of *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay as first described by Melton et al. (1984) was used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations by Myers and Maniatis (1985) and by Winter and Perucho (1985). In this type of RNase A mismatch cleavage assay, radiolabeled RNA probes transcribed in vitro from wild type sequences, are hybridized to complementary target regions derived from test samples. The test target generally comprises DNA (either genomic DNA or DNA amplified by cloning in plasmids or by PCR™), although RNA targets (endogenous mRNA) have occasionally been used (Gibbs and Caskey, 1987; Winter and Perucho, 1985). If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches (Ellis et al., 1994; Lishanski et al., 1994).

By hybridizing each strand of the wild type probe in RNase cleavage mismatch assays separately to the complementary Sense and Antisense strands of the test target, two different complementary mismatches (for example, A-C and G-U or G-T) and therefore two chances for detecting each mutation by separate cleavage events, was provided. Myers et al. (1985) used the RNase A cleavage assay to screen 615 bp regions of the human β-globin gene contained in recombinant plasmid targets. By probing with both strands, they were able to detect most, but not all, of the β-globin mutations in their model system. The collection of mutants included examples of all the 12 possible types of mismatches between RNA and DNA: rA/dA, rC/dC, rU/dC, rC/dA, rC/dT, rU/dG, rG/dA, rG/dG, rU/dG, rA/dC, rG/dT, and rA/dG.

Myers et. al. (1985) showed that certain types of mismatch were more frequently and more completely cleaved by RNase A than others. For example, the rC/dA, rC/dC, and rC/dT mismatches were cleaved in all cases, while the rG/dA mismatch was only cleaved in 13% of the cases tested and the rG/dT mismatch was almost completely resistant to cleavage. In general, the complement of a difficult-to-detect mismatch was much easier to detect. For example, the refractory rG/dT mismatch generated by probing a G to A mutant target with a wild type sense-strand probe, is complemented by the easily cleaved rC/dA mismatch generated by probing the mutant target with the wild type antisense strand. By probing both target strands, Myers and Maniatis (1986) estimated that at least 50% of all single-base mutations would be detected by the RNase A cleavage assay. These authors stated that approximately one-third of all possible types of single-base substitutions would be detected by using a single probe for just one strand of the target DNA (Myers et al., 1985).

In the typical RNase cleavage assays, the separating gels are run under denaturing conditions for analysis of the cleavage products. This requires the RNase to be inactivated by treating the reaction with protease (usually Proteinase K, often in the presence of SDS) to degrade the RNase. This reaction is generally followed by an organic extraction with a phenol/chloroform solution to remove proteins and residual RNase activity. The organic extraction is then followed by concentration and recovery of the cleavage products by alcohol precipitation (Myers et al., 1985; Winter et al., 1985; Theophilus et al., 1989).

4. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

5. Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

6. Kit Components

All the essential materials and reagents required for detecting a specific disease marker in a biological sample may be assembled together in a kit. This generally will comprise pre-selected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in Appendix A along with any other cDNAs for SENP1. In other embodiments preferred pairs of primers for amplification are selected to amplify any of the regions specified in Appendix A.

In another embodiment, such kits will comprise hybridization probes specific for SENP1, chosen from a group including nucleic acids corresponding to the sequence specified in Appendix A. Such kits generally will comprise, in suitable means, distinct containers for each individual reagent and enzyme as well as for each marker hybridization probe.

H. USE OF RNA FINGERPRINTING TO IDENTIFY DISEASE MARKERS

RNA fingerprinting is a means by which RNAs isolated from many different tissues, cell types or treatment groups can be sampled simultaneously to identify RNAs whose relative abundances vary. Two forms of this technology were developed simultaneously and reported in 1992 as RNA fingerprinting by differential display (Liang and Pardee, 1992; Welsh et al., 1992). (See also Liang and Pardee, U.S. Pat. No. 5,262,311, incorporated herein by reference in its entirety.) Some of the experiments described herein were performed similarly to Donahue et al., *J. Biol. Chem.* 269: 8604-8609, 1994.

All forms of RNA fingerprinting by PCR are theoretically similar but differ in their primer design and application. The most striking difference between differential display and other methods of RNA fingerprinting is that differential display utilizes anchoring primers that hybridize to the poly A tails of mRNAs. As a consequence, the PCR products amplified in differential display are biased towards the 3' untranslated regions of mRNAs.

The basic technique of differential display has been described in detail (Liang and Pardee, 1992). Total cell RNA is primed for first strand reverse transcription with an anchoring primer composed of oligo dT and any two of the four deoxynucleosides. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR techniques, utilizing the same primers. The resulting DNA fingerprint is analyzed by gel electrophoresis and ethidium bromide staining or autoradiography. A side by side comparison of fingerprints obtained from for example tumor versus normal tissue samples using the same oligonucleotide primers identifies mRNAs that are differentially expressed.

RNA fingerprinting technology has been demonstrated as being effective in identifying genes that are differentially expressed in cancer (Liang et al., 1992; Wong et al., 1993; Sager et al., 1993; Mok et al., 1994; Watson et al., 1994; Chen et al., 1995; An et al., 1995).

Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from patients. By determining that the concentration of a specific mRNA species varies, it is shown that the gene encoding the specific mRNA species is differentially expressed. This technique can be used to confirm that mRNA transcripts shown to be differentially regulated by RNA fingerprinting are differentially expressed in a particular disease.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

I. METHODS FOR SENP1 GENE EXPRESSION

In one embodiment of the present invention, there are provided methods for the increased SENP1 gene expression or activation in a cell. This is particularly useful where there is an aberration in the gene product or gene expression is not sufficient for normal function. This will allow for the alleviation of symptoms of disease experienced as a result of deficiency of SENP1. Further, given that SENP1 is a protease and that there is a great diversity of proteases and the myriad functions they perform, additional proteases may be implicated in this pathway. Specifically, one of the side effects of the long-term use of protease inhibitors in patients with AIDS is disease as the result. (Flexner, 1998). Thus, SENP1 gene expression could be increased or activated in such patients.

The general approach to increasing SENP1 activity according to the present invention, will be to provide a cell with an SENP1 polypeptide. While it is conceivable that the protein may be delivered directly, a preferred embodiment involves providing a nucleic acid encoding a SENP1 polypeptide, i.e., a SENP1 gene, to the cell. Following this provision, the SENP1 polypeptide is synthesized by the host cell's transcriptional and translational machinery, as well as any that may be provided by the expression construct. Cis-acting regulatory elements necessary to support the expression of the SENP1 gene will be provided, in the form of an expression construct. It also is possible that expression of virally-encoded SENP1 could be stimulated or enhanced, or the expressed polypeptide be stabilized, thereby achieving the same or similar effect.

In order to effect expression of constructs encoding SENP1 and other SENP1-like genes, the expression construct must be delivered into a cell. One mechanism for delivery is via viral infection, where the expression construct is encapsidated in a viral particle which will deliver either a replicating or non-replicating nucleic acid. In certain embodiments an HSV vector is used, although virtually any vector would suffice.

The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et. al., 1990), and receptor-mediated transfection (Wu and Wu, 1987; Wu and Wu, 1988). Some of these techniques may be successfully adapted for in vivo or ex vivo use, as discussed below.

In another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well. Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

Other expression constructs which can be employed to deliver a nucleic acid encoding a SENP1 transgene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994). Mannose can be used to target the mannose receptor on liver cells. Also, antibodies to CD5 (CLL), CD22 (lymphoma), CD25 (T-cell leukemia) and MAA (melanoma) can similarly be used as targeting moieties. In other embodiments, the delivery vehicle may comprise a ligand and a liposome.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk–, hgprt– or aprt– cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

J. METHODS FOR BLOCKING SENP1 ACTION

In another embodiment of the present invention, there is contemplated the method of blocking the function of SENP1 in disease. In this way, it may be possible to curtail the effects of excess SENP1 in disease. In addition, it may prove effective to use this sort of therapeutic intervention in combination with more traditional therapies.

The general form that this aspect of the invention will take is the provision, to a cell, of an agent that will inhibit SENP1 function. Four such agents are contemplated. First, one may employ an antisense nucleic acid that will hybridize either to the SENP1 gene or the SENP1 gene transcript, thereby preventing transcription or translation, respectively. The considerations relevant to the design of antisense constructs have been presented above. Second, one may utilize a SENP1-binding protein or peptide, for example, a peptidomimetic or an antibody that binds immunologically to SENP1. The binding of either will block or reduce the activity of the SENP1. The methods of making and selecting peptide binding partners and antibodies are well known to those of skill in the art. Third, one may provide to the cell an antagonist of SENP1, for example, an inhibitor, alone or coupled to another agent. Fourth, one may provide an agent that binds to the SENP1 substitute(s) without the same functional result as would arise with SENP1 binding.

Provision of a SENP1 gene, a SENP1 protein, or a SENP1 antagonist, would be according to any appropriate pharmaceutical route. The formulation, of such compositions and their delivery to tissues is discussed below. The method by which the nucleic acid, protein or chemical is transferred, along with the preferred delivery route, will be selected based on the particular site to be treated. Those of skill in the art are capable of determining the most appropriate methods based on the relevant clinical considerations.

Many of the gene transfer techniques that generally are applied in vitro can be adapted for ex vivo or in vivo use. For example, selected organs including the liver, skin, and muscle tissue of rats and mice have been bombarded in vivo (Yang et al., 1990; Zelenin et al., 1991). Naked DNA also has been used in clinical settings to effect gene therapy. These approaches may require surgical exposure of the target tissue or direct target tissue injection. Nicolau et al. (1987) accomplished successful liposome-mediated gene transfer in rats after intravenous injection.

Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. Thus, it is envisioned that DNA encoding an antisense construct also may be transferred in a similar manner in vivo.

Where the embodiment involves the use of an antibody that recognizes a SENP1 polypeptide, consideration must be given to the mechanism by which the antibody is introduced into the cell cytoplasm. This can be accomplished, for example, by providing an expression construct that encodes a single-chain antibody version of the antibody to be provided. Most of the discussion above relating to expression constructs for antisense versions of the SENP1 gene will be relevant to this aspect of the invention. Alternatively, it is possible to present a bifunctional antibody, where one antigen binding arm of the antibody recognizes a SENP1 polypeptide and the other antigen binding arm recognizes a receptor on the surface of the cell to be targeted. Examples of suitable receptors would be an HSV glycoprotein such as gB, gC, gD, or gH. In addition, it may be possible to exploit the Fc-binding function associated with HSV gE, thereby obviating the need to sacrifice one arm of the antibody for purposes of cell targeting. Advantageously, one may combine this approach with more conventional therapy options.

K. TRANSGENIC ANIMALS/KNOCKOUT ANIMALS

In one embodiment of the invention, transgenic animals are produced which contain a functional transgene encoding wild-type or SENP1 polypeptides. Transgenic animals expressing SENP1 transgenes, recombinant cell lines derived from such animals and transgenic embryos may be useful in methods for screening for and identifying agents that induce or repress function of SENP1. Such models will be useful in identifying new and novel agents that will be useful in a therapeutic context. Transgenic animals of the present invention also can be used as models for studying indications of abnormal SENP1 expression in.

In one embodiment of the invention, a SENP1 transgene is introduced into a non-human host to produce a transgenic animal expressing a human SENP1. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety). Additional descriptions for generating transgenic animal models may be found in numerous published Patents including but not limited to U.S. Pat. No. 5,817,912; U.S. Pat. No. 5,817,911; U.S. Pat. No. 5,814,716; U.S. Pat. No. 5,814,318; U.S. Pat. No. 5,811,634; U.S. Pat. No. 5,741,957; U.S. Pat. No. 5,731,489; U.S. Pat. No. 5,770,429; U.S. Pat. No. 5,718,883, each of these patents is specifically incorporated herein by reference as teaching methods and compositions for the production of transgenic animals.

It may be desirable to replace the endogenous SENP1 by homologous recombination between the transgene and the endogenous gene; or the endogenous gene may be eliminated by deletion as in the preparation of "knock-out" animals. Typically, a SENP1 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to rodents, reptiles, amphibians, birds, mammals, and fish. Within a particularly preferred embodiment, transgenic mice are generated which overexpress SENP1 or express a mutant form of the polypeptide. Alternatively, the absence of a SENP1 in "knock-out" mice permits the study of the effects that loss of SENP1 protein has on a cell in vivo. Knock-out mice also provide a model for the development of SENP1-related abnormalities.

As noted above, transgenic animals and cell lines derived from such animals may find use in certain testing experiments. In this regard, transgenic animals and cell lines capable of expressing wild-type or SENP1 may be exposed to test substances. These test substances can be screened for the ability to enhance wild-type SENP1 expression and/or function or impair the expression or function of SENP1.

L. PHARMACEUTICALS AND IN VIVO METHODS FOR THE TREATMENT OF DISEASE

Aqueous pharmaceutical compositions of, the present invention will have an effective amount of a SENP1 expression construct, an antisense SENP1 expression construct, an expression construct that encodes a therapeutic gene along with SENP1, a protein or compound that inhibits mutated SENP1 function respectively, such as an anti-SENP1 antibody. Such compositions generally will be dissolved or dispersed in a pharmaceutically acceptable carrier or aqueous medium. An "effective amount," for the purposes of therapy, is defined at that amount that causes a clinically measurable difference in the condition of the subject. This amount will vary depending on the substance, the condition of the patient, the type of treatment, the location of the lesion, etc.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredients, its use in the therapeutic compositions is contemplated. Supplementary active ingredients, such as other anti-diabetic agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains SENP1 inhibitory compounds alone or in combination with a conventional therapy agents as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In many cases, the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon-formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

M. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Specific Experimental Procedures

Cell Lines and Culture Conditions—COS-M6 cells were maintained in Dulbecco's modified Eagle's medium supplemented with 10% fetal calf serum and antibiotics.

Antibodies—16B12 (Babco, Richmond, Calif.) is a mouse monoclonal antibody to the peptide sequence YPYDVPDYA (SEQ ID NO:3) of influenza hemagglutinin (HA). Mouse anti-RH (specific for the amino acid sequence, RGSHHHH (SEQ ID NO:4)) monoclonal antibody was purchased from Qiagen (Santa Clara, Calif.).

Plasmid Construction and Transfection—The cDNA for ubiquitin, NEDD8, sentrin-1, sentrin-2, PML and RanGAP1 were subcloned into pcDNA3-HA vector as described previously (Kamitani et al., 1997a; Kamitani et al., 1997b). The full-length cDNA fragment for SENP1 was cloned into pcDNA3-RGH vector using standard techniques. The plasmids described above were transfected into COS cells using LipofectAMINE (Life Technologies, Inc.) described previously (Kamitani et al., 1997a; Kamitani et al., 1997b).

Western Blotting—Protein samples were treated at 45° C. for 1 h in 300 µl of 2% SDS treating solution containing 5%-mercaptoethanol. After SDS-polyacrylamide gel electrophoresis, Western blotting was performed using the protocol obtained from ECL detection system (Amersham Pharmacia Biotech). As secondary antibodies, horseradish peroxidase (HRP)-conjugated antibodies against mouse IgG or rabbit IgG (Santa Cruz Biotechnology, Santa Cruz, Calif.) were used.

cDNA cloning of the human SENP1—To identify the human proteases specific for sentrin conjugates, the inventors screened the EST databases by BLASTn sequence search using the amino acid sequence of HsUlp1 reported by Li et al. (Li and Hochstrasser, 1999). 70 EST sequences were identified in the initial screen. After further analysis, three EST sequences (AI148063, A1261629 and N36589) were found to overlap partially. Following extensive PCR™ and 5'-RACE, a full-length (1113 bp) HsUlp1 was elucidated. The HsUlp1 sequence was used to identify additional sequences from the GenBank, including a 193 kb human genomic DNA fragment (Accession number: AC004801) that contains a 200 bp region homologous, but not identical, to HsUlp1. Further analysis of the 193 kb human genomic DNA by the exon trapping technique resulted in the identification of a region with high homology to the conserved region of HsUlp1 (den Dunnen, 1999). Primers were designed based on the information obtained from the genomic DNA sequences. PCR™ amplification with primer-1 (5'-CATTTTAACTAACCAGGAA-CAGCTGTCC-3' (SEQ ID NO:5)corresponding to AA258-266) and primer-2 (5'-CAAGAGTTTTCGGTGGAGGATCTCC-3' (SEQ ID NO:6) corresponding to AA636-643) resulted in the production of a 1.1 kb cDNA fragment from the human placenta cDNA library. The coding region of the cloned cDNA was extended using 5'-RACE PCR™. Using a pair of redesigned 5' and 3' primers compatible with the sequence revealed in the 5' and 3' anchored PCR™ reactions, a 2.5 kb cDNA fragment, which encodes the SENP1 protein, was amplified by PCR™.

PCR™, 5'-RACE, and Sequence Analysis—The nested primers were synthesized on the basis of the information obtained from either the positive EST clones or from the genomic DNA. These primers were used to amplify the novel protease gene fragments by PCR™ from a human placenta cDNA library. Both PCR™ and RACE were performed as described previously (Gong and Yeh, 1999). The nucleotide sequences were determined using dye terminator sequencing and an automated sequencer from Applied Biosystems Inc. (Foster City, Calif.).

Example 2 cDNA Cloning and Genomic Organization of SENP1

Figure 1:
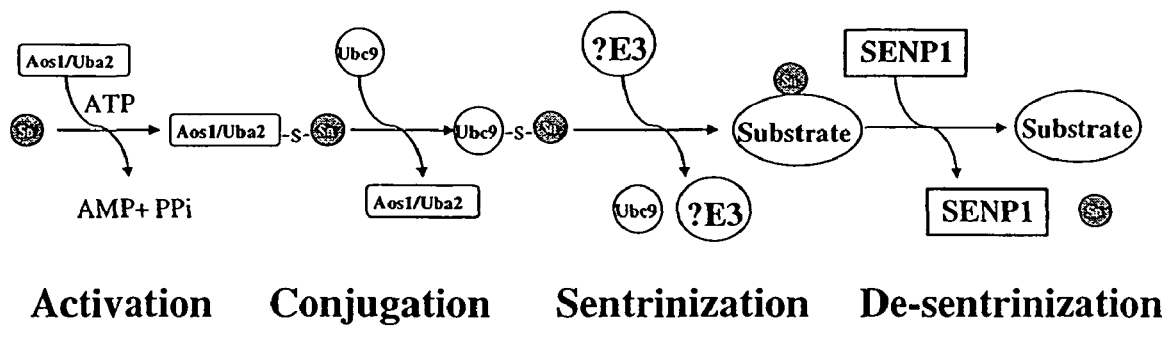
FIG. 1. The sentrinization and de-sentrinization pathway.

Li et al. recently reported a novel protease, Ulp1, specific for Smt3, the yeast homologue of sentrin-1. In the same report, a human EST sequence homologous to Ulp1 was tentatively termed HsUlp1 (Li and Hochstrasser, 1999). Using a combined PCR™ cloning and data base search technique described previously (Gong et al., 1999; Gong and Yeh, 1999), the inventors identified full length HsUlp1, which encodes a 371 aa protein (FIG. 1). However, extensive studies indicated that HsUlp1 had no activity against sentrin-modified proteins.

When full-length HsUlp1 sequence was used as query to do a BLASTn sequence search, the inventors detected a conserved region of 200 bp from a 193 kb human genomic DNA fragment (Accession number: AC004801). This 200 bp region shows ~56% identity with amino acids 202-265 of HsUlp1, and contains one conserved histidine residue present in all Ulp1-related proteins from different species (Li and Hochstrasser, 1999). Further analysis of the 193 kb genomic DNA by the exon trapping technique resulted in the discovery of another region that contains one conserved cysteine residue. To determine whether this genomic DNA encodes a functional protein, the inventors amplified a small DNA fragment from a human placenta cDNA library with PCR™. The primers were designed based on the information obtained from exon trapping of the 193 kb genomic DNA. Extension of the cloned cDNA by RACE resulted in the identification of a 2511 bp cDNA clone from a human placenta cDNA library. The 2511 bp cDNA clone. (SEQ ID NO:1)contains an ORF of 1929 bp, encoding a protein of 643 amino acids (SEQ ID NO:2) (FIG. 1). The predicted coding region of this ORF is preceded by an in-frame stop codon and has a consensus sequence commonly associated with initiation methionines (Kozak, 1991). The protein encoded by this ORF was named SENP1 (sentrin-specific protease-1) because it possesses a protease activity against sentrin-modified proteins, but not ubiquitin or NEDD8-modified proteins in vivo (see below).

As shown in FIG. 3, SENP1 is 21% identical and 50% similar to yeast Ulp1. The similarity among SENP1, HsUlp1, and yeast Ulp1 is confined primarily to the C-terminal region of ~200 amino acids, within which a ~90-residue segment has been proposed to form a core structure common to a diverse and widespread group of cysteine proteases (Li and Hochstrasser, 1999). Similar to yeast Ulp1, both SENP1 and HsUlp1 have four conserved catalytic residues of an adenoviral protease. Both SENP1 and yeast Ulp1 are similar in size. In contrast, the amino acid sequence of HsUlp1 is much shorter than yeast Ulp1 and human SENP1, suggesting that the N-terminal sequences play an important role in the protease activity against Smt-3 or sentrin-1.

The SENP1 gene was found to be located in 12q13.1 and spanned about 61 kb of contiguous DNA (FIG. 4). The SENP1 gene is composed of 18 distinct exons ranging between 39 and 487 bp. Both the 5' and 3' acceptor splice sites in each of the introns followed the GT-AG consensus sequence for eukaryotic genes (FIG. 2). Both exon 1 (112 bp) and exon 2 (47 bp) encoded most of the 5'-untranslated region, whereas exon 3 contained the remaining 14 bp of the 5'-untranslated region plus the first 36 amino acids. Exons 5 through 17 encoded most of amino acids, with exon 18 (~487 bp) containing the final 20 codons and an extensive 3'-untranslated region of ~423 bp.

Example 3

SENP1 is a Sentrin-Specific Protease

A COS cell expression system was used to demonstrate the activity of SENP1 in vivo. Briefly, HA-tagged sentrin-1 was introduced into COS cells by liposome-mediated transfection. Total cell lysates were prepared 16 hr after transfection for Western blot analysis using anti-HA antibody. As shown in FIG. 5A lane 1, a 90 kDa band and higher molecular weight sentrin-1 conjugates were detected. When HA-tagged sentrin-1 was co-expressed with His-tagged SENP1, the higher molecular weight sentrin-1 conjugates were completely removed (lane 2). However, the 90 kDa band, which most likely represents sentrinized RanGAP1, remained intact. The disappearance of the high molecular weight sentrin-1 conjugates also coincided with the accumulation of free sentrin-1 monomers. A similar pattern was observed when myc-tagged SENP1 was co-expressed with HA-tagged sentrin-1 (lane 3). The activity of SENP1 is restricted to sentrin-1 because it did not appear to have any activity against ubiquitin-modified proteins (lanes 4, 5, 6). FIG. 5B shows that SENP1 is also active against sentrin-2 modified proteins. Again, the 90 kDa band was not affected by SENP1, and the sentrin-2 monomer accumulated in COS cells over-expressing His-tagged SENP1. The inventors also tested the activity of SENP1 against NEDD8-modified proteins. As expected, SENP1 was unable to affect NEDD8 conjugates (FIG. 5C). Taken together, SENP1 is a sentrin-specific protease that selectively removes sentrin from sentrinized proteins.

Example 4

SENP1 Processes Sentrinized PML, but not Sentrinized RanGAP1

The inability of SENP1 to reduce the 90 kDa band suggests that SENP1 cannot remove sentrin from all sentrinized proteins. Thus, the inventors tested the effect of SENP1 on two specific sentrin conjugates, RanGAP1 and PML. RanGAP1 is a 70 kDa cytosolic protein that can be modified by a single molecule of sentrin-1 (Matunis et al., 1998; Mahajian et al., 1998). Sentrinized RanGAP (90 kDa) is a component of the nuclear pore complex and plays a role in regulating nuclear transport. When HA-tagged RanGAP1 was expressed in COS cells, a 70 kDa un-modified form of RanGAP1 and a 90 kDa band corresponding to sentrinized RanGAP1 were observed (FIG. 6, lane 1). Co-expression of SENP-1 was unable to remove native sentrin from HA-tagged RanGAP1 (lane 2). This is consistent with the results shown in FIGS. 5A and 5B, which show that the 90 kDa band is resistant to SENP1. Li et al. have shown that SUMO-1 (sentrin-1)-modified RanGAP1 could be cleaved by Ulp1 using an in vitro assay. The difference between the inventors' in vivo results and Li's in vitro data is best explained by the observation that SENP1 is localized in the nucleus. Thus, the nuclear localized SENP1 does not have access to sentrinized RanGAP1, which is attached to the cytoplasmic fibrils of the nuclear pore complex This interpretation is also supported by the inventors' previous finding that the majority of high molecular weight sentrinized proteins, which are sensitive to SENP1 (FIG. 5A, and FIG. 5B), are localized in the nucleus (Kamitani et al., 1997a; Kamitani et al., 1997b). In order to test this hypothesis further, the inventors study the in vivo activity of SENP1 against a well-studied nuclear protein, PML. As expected, native sentrin was completely removed from sentrinized PML in COS cells expressing His-tagged SENP1 (FIG. 4, lane 4).

PML, a RING finger protein with tumor suppressor activity, has been implicated in the pathogenesis of acute promyelocytic leukemia that arises following a reciprocal chromosomal translocation that fuses the PML gene with the retinoic acid receptor γ (RARγ) gene (Melnick and Licht, 1999). In acute promyelocytic leukemia, two forms of PML-RARγ fusion proteins have been reported. Remarkably, both forms of PML-RARγ fusion proteins could not be sentrinized in vivo (Kamitani et al., 1998c).

Example 5

Elucidation of the Role of SENP1 in Regulating PML

Studies to further elucidate the role of SENP1 in regulating the biological function of PML and in the pathogenesis of acute promyelocytic leukemia, may be performed using the methods described above. Those of skill in the art will be able to design and undertake such studies in view of the teachings of this specification.

Example 6

Additional SENP Members

Six additional Sentrin-specific proteases have been identified. Though of variable lengths, each human Sentrin-specific protease has the conserved C-terminal region. Their similarity with yeast Ulp1 is limited mainly to the C-terminal region of approximately 200 amino acids (FIG. 7).

Like yeast Ulp1, these Sentrin-specific proteases possess four conserved catalytic residues of an adenoviral protease. Their C-termini contain the catalytic domain while their N-termini are involved in substrate specificity and cellular localization. The nucleic acid and protein sequences of SENP2 are shown in SEQ ID NO:7 and 8, respectively. SenP2 has 509 amino acids and it was able to remove Sentrin-1 from the higher molecular weight Sentrin-1 conjugates. Sentrinized PML, a tumor suppressor that resides in the nucleus, was selectively affected by SENP2, whereas sentrinized RanGAP remained intact.

SENP3 has 568 amino acid residues. It appears to be located only in the nucleolus, while SENP1 is in the nucleus, but not nucleolus; SENP2 has been observed in both locations. A comparison of the amino acid sequences of SENP1, SENP2, and SENP3 is shown in Table 5.

TABLE 5

```
              *                      *         *         *
SENP1   MDDIA---DRMRMDAGEVTLVNHNSVFKTHLLPQTGFPEDQLSLSDQQILSSRQGHLDRS    57
SENP2   MVTSACNGTRNVAPSGEV-----FSNSSSCELTGSGSWNNMLKLGNKS------------    42
SENP3   MKETI-QGTGSWGPEPPG-PGTAYSNPRRDGLRWPLPPKPRLKSGGGFGPDPGSG-----    54
                                 *              *     *    *    *
SENP1   FTCST-RSAAYNPSYYSDNPSSDSFLGSGDLRTFGQSANGQWRNSTPSSSSSLQKSRNSR   116
SENP2   -----------PNGISDYPKIRVTV-TRD----------QPRRVLPSFGFTLN------    74
SENP3   TTVPTRRLPAPRPSFDASASEEEEEEEEEDEEEVAA-----WR--LPPRWGQLGASQRSR   106
                  *                                        *    *
SENP1   SLYLET--RKTSSGLSNSFAGKSNHHCHVSAYEKSFPIKPVPSPSWSGSCRRSLLSPKKT   173
SENP2   -----------SEGCNRRPGGRRHSKGNPESSLM--WKPQEQAVTEMI---SEESGKG-   116
SENP3   ALRLRPSHRKTCSQRRRRAMRAFQMLLYSKSTSLTFHWKLWGRHRGR---RRGLAHFKNH   161
        **   *  ** ** **** ** **                 *      *         ** *
SENP1   QRRHVSTAEETVQEEEREIYRQLLQMVTGKQFTIAKPTTHFPLHLSRCLSSSKNTLKDSL   234
SENP2   LRRPHCTVEEGVQKEEREKYRKLLE----RLKESGHGNSVCPVT-SNYH-SSQRSQMDTL   170
SENP3   LSPQQATPQVPSPCCRFDSPRGPPPP---RLGLLGALMAEDGVRGSPPVPSGPPMEEDGL   221
                     *                           *       *    *   *
SENP1   FKNGNSCASQIIGSDTSSSGSASILTNQEQLSHSVYSLSSYTPDVAFGSKDSGTLHHPHH   294
SENP2   -KTKGWGEEQNHGVKTTQFV------------------PKQYRLVETRG----PLC    203
```

TABLE 5-continued

```
SENP3  RWTPKSPLDPDSGLLSCTL---------------------PN-GFGGQ-SG----PEG  250
                         *  *         *                    *
SENP1  HHSVPHQPDNLAASNTQSEGSDSVILLKVKDSQTPTPSSTFFQAELWIKELTSVYDSRAR  354
SENP2  ---------SLRSEKRCSKGKITDTEKMV----------GIRFENESRRGY--------  235
SENP3  ERSLAPPDASILISNVCSIGDH------VAQELFQG-SDLGMAEEAE-RPGE--------  297
                *    * *       *                  *           *
SENP1  ERLRQIEEQKALALQLQNQRLQEREHS-VHDSVELHL--RVPLEKEIPVTVVQETQKKGH  411
SENP2  --------------QLE-PDLSEE----VSARLRLGSGSNGLLRRKVSIIETKEKNCSGK  276
SENP3  ---------KA--GQHS-P-LREEHVTCVQSILDEFLQTYGSLIP-LSTDEVVEKLEDIF  341
                  *   * ** ***** *      * *** ** ** * *** *****     ****
SENP1  KLTDSEDEFPEITEEMEKEIKNVFRNGNQDEVLSEAFRLTITRKDIQTLNHLNWLNDEII  471
SENP2  ERDRRTDDLLELTEDMEKEISNALGHGPQDEILSSAFKLRITRGDIQTLKNYHWLNDEVI  336
SENP3  QQEFSTPSRKGLVLQLIQSYQRMPGNAMVRGFRVAYKRHVLTMDDLGTLYGQNWLNDQVM  401
              **              *  *  **    **     **   ******    *    * ***
SENP1  NFYMNNLMERSKEKGLPSVHAFNTFFFTKLKTAGYQAVKRWTKKVDVFSVDILLVPIHLG  331
SENP2  NFYMNLLVERNKKQGYPALHVFSTFFYPKLKSGGYQAVKRWTKGVNLFEQEIILVPIHRK  396
SENP3  ---MNMYGDLVMDTVPEKVHFFNSFFYDKLRTKGYDGVKRWTKNVDIFNKELLLIPIHLE  357
       ***  *     *       * **               ** *   *        *
SENP1  VHWCLAVVDFRKKNITYYDSMGGINNEACRILLQYLKQESIDKKRKEFDTNGWQLFS-KK  574
SENP2  VHWSLVVIDLRKKCLKYLDSNGQKGHRICEILLQYLQDESKTKRNSDLNLLEWTHHSMKP  456
SENP3  VHWSLISVDVRRRTITYFDSQRTLNRRCPKHIAKYLQAEAVKKDRLDFHQ-GWKGYF-KM  515
       * *  ****  *      *         * *** **         *   *  *
SENP1  SQIPQQMNGSDCGMFACKYADCITKDRPINFTQQHMPYFRKRMVWEILHRKLL         643
SENP2  HEIPQQLNGSDCGMFTCKYADYISRDKPITFTQHQMPLFRKKMVWEILHQQLL         509
SENP3  N-VARQNNDSDCGAFVLQYCKHLALSQPFSFTQQDMPKLRRQIYKELCHCKLTV        568
                      * * * * * * * *
```

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,215,051
U.S. Pat. No. 4,554,101
U.S. Pat. No. 4,683,195
U.S. Pat. No. 4,683,202
U.S. Pat. No. 4,800,159
U.S. Pat. No. 4,873,191
U.S. Pat. No. 4,883,750
U.S. Pat. No. 4,946,773
U.S. Pat. No. 5,262,311
U.S. Pat. No. 5,279,721
U.S. Pat. No. 5,718,883
U.S. Pat. No. 5,731,489
U.S. Pat. No. 5,741,957
U.S. Pat. No. 5,770,429
U.S. Pat. No. 5,811,634
U.S. Pat. No. 5,814,318
U.S. Pat. No. 5,814,716
U.S. Pat. No. 5,817,911
U.S. Pat. No. 5,817,912
EPA No. 329 822
GB Application No. 2,202,328
PCT/US87/00880
PCT/US89/01025
WO 84/03564
WO 88/10315
WO 89/06700
WO 90/07641
An et al., *Proc. Ameri. Assn. Canc. Res.*, 36:82, 1995.
Baichwal and Sugden, In: Kucherlapati R, ed. Gene transfer. New York: Plenum Press, pp. 117-148, 1986.
Bellus, *J. Macromol. Sci. Pure Appl. Chem*, A31(1): 1355-1376, 1994.
Benvenisty and Neshif, *Proc. Nat'l. Acad. Sci. USA*, 83:9551-9555, 1986.
Bittner et al., *Methods in Enzymol*, 153:516-544, 1987.
Boddy et al., *Oncogene*, 13:971-982, 1996.
Brinster et al., *Proc. Nat'l Acad. Sci. USA*, 82: 4438-4442, 1985.
Buschmann et al., *Cell.* 101:753-62, 2000.
Capaldi et al., *Biochem. Biophys. Res. Comm.*, 76:425, 1977.
Chen and Okayama, *Mol. Cell Biol.*, 2745-2752, 1987.
Chen et al., *Proc. Am. Urol. Assn.*, 153:267A, 1995.
Colberre-Garapin et al., *J. Mol. Biol.*, 150: 1, 1981.
Cotton, *Biochem J.*, 263:1-10, 1989.
Coupar et al., *Gene*, 68:1-10, 1988.
den Dunnen, *Methods Enzymol.*, 303:100-110, 1999.
Desterro et al., *Mol. Cell*, 2:233-239, 1998.
Donahue et al., *J. Biol. Chem.*, 269:8604-8609, 1994.
Dubensky et al., *Proc. Nat'l Acad. Sci. USA*, 81:7529-7533, 1984.
Ellis, L. A. et al., *Nucleic Acids Res.*, 22:2710-2711, 1994.
Fechheimer et al., *Proc. Nat'l Acad Sci. USA*, 84:8463-8467, 1987.
Ferkol et al., *FASEB J.*, 7:1081-1091, 1993.
Flexner, *N. Engl. J. Med.*, 338:1281-1292, 1998.
Fraley et al., *Proc. Natl. Acad. Sci. USA*, 76:3348-3352, 1979.
Freifelder, *Physical Biochemistry Applications to Biochemistry and Molecular Biology*, $2^{nd}$ ed. WM. Freeman and Co., New York, N.Y., 1982.

Freshney, Second Edition, Oxford/New York, IRL Press, Oxford University Press, 1992.
Friedmann, *Science*, 244:1275-1281, 1989.
Frohman, M. S., In: *PCR Protocols: a Guide to Methods and Applications*, Academic Press, N.Y., 1990.
Gefter et al., *Somatic Cell Genet.*, 3: 231-236, 1977.
Ghosh and Bachhawat, In: Wu G. and C. Wu ed. Liver diseases, targeted diagnosis and therapy using specific receptors and ligands. New York: Marcel Dekker, pp. 87-104, 1991.
Gibbs and Caskey, *Science*, 236:303-305, 1987.
Goding, 1986, In Monoclonal Antibodies: Principles and Practice, 2d ed., Orlando, Fla., Academic Press, 1986, pp. 60-61, 65-66, and 71-74.
Gong and Yeh, *J. Biol. Chem.*, 274:12036-12042, 1999.
Gong et al., *J. Biol. Chem.*, 272:28198-28201, 1997.
Gong et al., *FEBS Letter*, 448:185-189, 1999.
Gong et al., *J. Biol. Chem.*, 275:3355-3359, 2000.
Gopal, *Mol. Cell Biol.*, 5:1188-1190, 1985.
Graham and van der Eb, *Virology*, 52:456-467, 1973.
Harland and Weintraub, *J. Cell Biol.*, 101:1094-1099, 1985.
Harlow and Lane, Antibodies: A Laboratory Manual, Cold Spring Harbor Laboratory, 1988.
Hershko and Ciechanover, *Annu. Rev. Biochem.*, 67:425-479, 1998.
Hermonat and Muzyczka, *Proc. Nat'l Acad. Sci. USA*, 81:6466-6470, 1984.
Hess et al., *J. Adv. Enzyme Reg.*, 7:149, 1968.
Hitzeman et al., *J. Biol. Chem.*, 255:2073, 1980.
Hogan et al., eds., Manipulating the Mouse Embryo: A Laboratory Manual, 2nd ed., Cold Spring Harbor Laboratory Press, 1994.
Holland et al., *Biochemistry*, 17:4900, 1978.
Horwich et al. *J. Virol.*, 64:642-650, 1990.
Innis et al., *PCR™ Protocols*, Academic Press, Inc., San Diego Calif., 1990.
Inouye et al., *Nucleic Acids Res.*, 13: 3101-3109, 1985.
Johnson et al., "Peptide Turn Mimetics" in *BIOTECHNOLOGY AND PHARMACY*, Pezzuto et al., Eds., Chapman and Hall, New York 1993.
Jones, *Genetics*, 85: 12, 1977.
Kamitani et al., *J. Biol. Chem.*, 274:11349, 1998a.
Kamitani et al., *J. Biol. Chem.*, 273:26675-26682, 1998b.
Kamitani et al., *J. Biol. Chem.*, 273:3117-3120, 1998c.
Kamitani et al., *J. Biol. Chem.*, 272:14001-14004, 1997a.
Kamitani et al., *J. Biol. Chem.*, 272:28557-28562, 1997b.
Kaneda et al., *Science*, 243:375-378, 1989.
Kato et al., *J. Biol. Chem.*, 266:3361-3364, 1991.
Kawabe et al., *J. Biol Chem.* 275:20963-20966, 2000.
Kim et al., *J. Biol Chem.* 275:14102-6,2000.
Kingsman et al., *Gene*, 7: 141 1979.
Klein et al., *Nature*, 327:70-73, 1987.
Kohler and Milstein, *Eur. J. Immunol.*, 6:511-519, 1976.
Kohler and Milstein, *Nature*, 256:495-497, 1975.
Kozak, *J. Biol. Chem.*, 266:19867-19870, 1991.
Kwoh et al., *Proc. Natl. Acad. Sci. USA*, 86:1173, 1989.
Kyte and Doolittle, *J. Mol. Biol.*, 157(1):105-132, 1982.
Li and Hochstrasser, *Nature* 398, 246-251, 1999.
Liang and Pardee, *Science*, 257:967-971, 1992.
Lishanski et la., *Proc. Natl. Acad. Sci USA*, 91:2674-2678, 1994.
Lowry et al., *Cell*, 22: 817, 1980.
Mahajan et al., *Cell*, 88:97-107, 1997.
Mahajian et al., *J. Cell Biol.*, 140:259-270, 1998.
Mao et al., *Proc Natl Acad Sci USA.* 97:4046-51, 2000a.
Mao et al., *J. Biol Chem.*, 2000b Jun. 20.
Matunis, Coutavas, Blobel, *J. Cell Biol.*, 135:1457-1470, 1996.
Matunis et al., *J. Cell Biol.* 140, 499-509, 1998.
Melnick and Licht, *Blood* 93:3167-215, 1999.
Melton et al, *Nucleic Acid Res.*, 12:7035-7056, 1984.
Mok et al., *Gynecol. Oncol.*, 52:247-252, 1994.
Muller and Dejean, *J. Virol.* 73:5139, 1999.
Muller et al., *EMBO J.*, 17:61-70, 1998.
Mulligan et al., *Proc. Nat'l Acad. Sci. USA*, 78: 2072, 1981.
Myers and Maniatis, *Cold Spring Harbor Symposium on Quantitative Biology*, Vo. LI, pp. 18275-18284, 1986.
Myers and Maniatis, *Science*, 230:1242-1246, 1985.
Nicolas & Rubenstein, In: *Vectors: A survey of molecular cloning vectors and their uses*, Rodriguez & Denhardt (eds.), Stoneham: Butterworth, pp. 493-513, 1988.
Nicolau and Sene, *Biochem. Biophys. Acta*, 721:185-190, 1982.
Nicolau et al., *Methods Enzymol.*, 149:157-176, 1987.
Ohara et al., *Proc. Nat'l Acad. Sci. USA*, 86: 5673-5677, 1989.
O'Hare et al., *Proc. Nat'l Acad. Sci. USA*, 78: 1527, 1981.
Okura et al., *J. Immunol.*, 157, 4277-4281, 1996.
Perales et al., *Proc. Natl., Acad. Sci. USA*, 91:4086-4090, 1994.
Potter et al., *Proc. Natl. Acad. Sci. USA*, 81:7161-7165, 1984.
Rangasamy et al., *J. Biol. Chem.* 2000, Jun. 27.
*Remington's Pharmaceutical Sciences*, 15th Edition, Chapter 61, pages 1035-1038 and 1570-1580.
Ridgeway, In: Rodriguez R L, Denhardt D T, ed. Vectors: A survey of molecular cloning vectors and their uses. Stoneham: Butterworth, pp. 467-492, 1988.
Rippe et al., *Mol. Cell. Biol.*, 10:689-695, 1990.
Sager et al., *FASEB J.*, 7:964-970, 1993.
Saitoh et al., *Current Biol.*, 8:121-124, 1998.
Sambrook et al., *Molecular Cloning: A Laboratory Manual*, 2d Ed., Cold Spring Harbor Laboratory Press, cold Spring Harbor, N.Y., 1989.
Sternsdorf et al., *J. Cell Biol.*, 139:1621-1634, 1997.
Stinchcomb et al., *Nature*, 282: 39, 1979.
Summers and Smith, "A manual of methods for baculovirus vectors and insect cell culture procedures," *Texas Agricultural Experiment Station Bulletin No.* 1555, 1987.
Szybalska et al., *Proc. Nat'l Acad. Sci. USA*, 48: 2026, 1962.
Temin, In: *Gene Transfer*, Kucherlapati (ed.), New York: Plenum Press, pp. 149-188, 1986.
Theophilus et al, *Nucleic Acids Research*, 17:7707-7722, 1989.
Tschemper et al., *Gene*, 10:157, 1980.
Tur-Kaspa et al., *Mol. Cell Biol.*, 6:716-718, 1986.
Wagner et al., *Science*, 260:1510-1513, 1990.
Wagner et al., *Science*, 260:1510-1513, 1993.
Walker et al., *Proc. Natl. Acad. Sci. USA*, 89:392-396, 1992.
Watson et al., *Cancer Res.*, 54:4598-4602, 1994.
Welsh et al., *Nucleic Acids Res.*, 20: 4965-4970, 1992.
Wigler et al., *Proc. Nat'l Acad. Sci. USA*, 77:3567, 1980.
Wigler et al., *Cell*, 11: 223, 1977.
Wilkinson, *FASEB J.*, 11:1245-1256, 1997.
Winter and Perucho, *Proc. Natl. Acad. Sci. USA*, 82:7575-7579, 1985.
Wong et al., *Int. J. Oncol.*, 3:13-17, 1993.
Wong et al., *Gene*, 10:87-94, 1980.
Wu and Wu, *Biochemistry*, 27:887-892, 1988.
Wu and Wu, *J. Biol. Chem.*, 262:4429-4432, 1987.
Wu and Wu, *Adv. Drug Delivery Rev.*, 12:1591-67, 1993.
Wu et al., *Genomics*, 4:560, 1989.
Yang et al., *Proc. Natl., Acad. Sci. USA*, 87:9568-9572, 1990.
Yeh et al., *Gene*, 248:1-14, 2000.
Zelenin et al., *FEBS Lett.*, 280:94-96, 1991.

What is claimed is:

1. An isolated polypeptide comprising the amino acid sequence of SEQ ID NO:2 or NO:8.

2. The isolated polypeptide of claim 1, wherein the polypeptide comprises SEQ ID NO: 2.

3. The isolated polypeptide of claim 1, wherein the polypeptide comprises SEQ ID NO: 8.

* * * * *

UNITED STATES PATENT AND TRADEMARK OFFICE
CERTIFICATE OF CORRECTION

PATENT NO. : 7,588,927 B2  Page 1 of 1
APPLICATION NO. : 10/624945
DATED : September 15, 2009
INVENTOR(S) : Edward T. H. Yeh et al.

It is certified that error appears in the above-identified patent and that said Letters Patent is hereby corrected as shown below:

In title page, item (73) Assignees, delete
"National Institutes of Health (NIH), Washington, DC (US); The United States of America as represented by the Department of Health and Human Services, Washington DC (US); U.S. Government NIH Divisional of Extramural Inventions and Technology Resources (DEITR), Washington, DC (US)"
and insert
--Board of Regents, The University of Texas System, Austin, TX (US)-- therefor.

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,588,927 B2 | Page 1 of 1 |
| APPLICATION NO. | : 10/624945 | |
| DATED | : September 15, 2009 | |
| INVENTOR(S) | : Yeh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 696 days.

Signed and Sealed this

Second Day of November, 2010

David J. Kappos
*Director of the United States Patent and Trademark Office*

SEQUENCE LISTING

<160> NUMBER OF SEQ ID NOS: 10

<210> SEQ ID NO 1
<211> LENGTH: 2512
<212> TYPE: DNA
<213> ORGANISM: Human

<400> SEQUENCE: 1

| | | | | | | |
|---|---|---|---|---|---|---|
| acctagcgac | tcttccggtg | ctgtgaaggc | ggttccggtt | cgcggcggtt | cccgggtttt | 60 |
| gcgttccgcg | cccggccgga | aaccccttcg | catggcagcc | ggttccggtt | cggactttgt | 120 |
| atctttgcta | aagtcagtga | tgtgaaaaga | cttgaaatgg | atgatattgc | tgataggatg | 180 |
| aggatggatg | ctggagaagt | gactttagtg | aaccacaact | ccgtattcaa | aacccacctc | 240 |
| ctgccacaaa | caggttttcc | agaggaccag | ctttcgcttt | ctgaccagca | gattttatct | 300 |
| tccaggcaag | gacatttgga | ccgatctttt | acatgttcca | caagaagtgc | agcttataat | 360 |
| ccaagctatt | actcagataa | tccttcctca | gacagttttc | ttggctcagg | cgatttaaga | 420 |
| acctttggcc | agagtgcaaa | tggccaatgg | agaaattcta | ccccatcgtc | aagctcatct | 480 |
| ttacaaaaat | caagaaacag | ccgaagtctt | tacctcgaaa | cccgaaagac | ctcaagtgga | 540 |
| ttatcaaaca | gttttgcggg | aaagtcaaac | catcactgcc | atgtatctgc | atatgaaaaa | 600 |
| tcttttccta | ttaaacctgt | tccaagtcca | tcttggagtg | gttcatgtcg | tcgaagtctt | 660 |
| ttgagcccca | agaaaactca | gaggcgacat | gttagtacag | cagaagagac | agttcaagaa | 720 |
| gaagaaagag | agatttacag | acagctgcta | cagatggtca | cagggaaaca | gtttactata | 780 |
| gccaaaccca | ccacacattt | tcctttacac | ctgtctcgat | gtcttagttc | cagtaaaaat | 840 |
| actttgaaag | actcactgtt | taaaaatgga | aactcttgtg | catctcagat | cattggctct | 900 |
| gatacttcat | catctggatc | tgccagcatt | ttaactaacc | aggaacagct | gtcccacagt | 960 |
| gtatattccc | tatcttctta | taccccagat | gttgcatttg | gatccaaaga | ttctggtact | 1020 |
| cttcatcatc | cccatcatca | ccactctgtt | ccacatcagc | cagataactt | agcagcttca | 1080 |
| aatacacaat | ctgaaggatc | agactctgtg | attttactga | aagtgaaaga | ttcccagact | 1140 |
| ccaactccca | gttctacttt | cttccaggca | gagctgtgga | tcaaagaatt | aactagtgtt | 1200 |
| tatgattctc | gagcacgaga | aagattgcgc | cagattgaag | aacagaaggc | attggcctta | 1260 |
| cagcttcaaa | accagagatt | gcaggagcgg | gaacattcag | tacatgattc | agtagaacta | 1320 |
| catcttcgtg | tacctcttga | aaaggagatt | cctgttactg | ttgtccaaga | aacacaaaaa | 1380 |
| aaaggtcata | aattaactga | tagtgaagat | gaatttcctg | aaattacaga | ggaaatggag | 1440 |
| aaagaaataa | agaatgtatt | tcgtaatggg | aatcaggatg | aagttctcag | tgaagcattt | 1500 |
| cgcctgacca | ttacacgcaa | agatattcaa | actctaaacc | atctgaattg | gctcaatgat | 1560 |
| gagatcatca | atttctacat | gaatatgctg | atggagcgaa | gtaaagagaa | gggcttgcca | 1620 |
| agtgtgcatg | catttaatac | cttttcttc | actaaattaa | aaacggctgg | ttatcaggca | 1680 |
| gtgaaacgtt | ggacaaagaa | agtagatgta | ttttctgttg | acattctttt | ggtgcccatt | 1740 |
| cacctgggag | tacactggtg | tctagctgtt | gtggacttta | gaagaagaa | tattacctat | 1800 |
| tacgactcca | tgggtgggat | aaacaatgaa | gcctgcagaa | tactcttgca | atacctaaag | 1860 |
| caagaaagca | ttgacaagaa | aaggaaagag | tttgacacca | atggctggca | gcttttcagc | 1920 |
| aagaaaagcc | agattcctca | gcagatgaat | ggaagtgact | gtgggatgtt | tgcctgcaaa | 1980 |
| tatgctgact | gtattaccaa | agacagacca | atcaacttca | cacagcaaca | catgccatac | 2040 |

```
ttccggaagc ggatggtctg ggagatcctc caccgaaaac tcttgtgaag actgtctcac    2100
ttagcagacc ttgaccatgt gggggaccag ctctttgttg tctacagcca gagaccttgg    2160
aaacagctgc tcccagccct ctgctgttgt aacacccttg atcctggacc aggccctggc    2220
gagatgcatt cacaagcaca tctgcctttc cttttgtatc tcagatacta ttttttgcaaa   2280 gaaactttgg tgctgtgaaa ggggtgaggg acatccctaa gctgaagaga gagactgctt    2340
ttcacttctt cagttctgcc atcttgtttt caaagggctc cagcctcact cagtccctaa    2400
ttatgggact gagaaaagct tggaaagaat cttggtttca tataaattct tgttgttagg    2460
ccttactaag aagtaggaaa gggcatgggc aaaaggtagg gataaaaacc ac            2512
```

<210> SEQ ID NO 2
<211> LENGTH: 643
<212> TYPE: PRT
<213> ORGANISM: Human

<400> SEQUENCE: 2

```
Met Asp Asp Ile Ala Asp Arg Met Arg Met Asp Ala Gly Glu Val Thr
1               5                   10                  15

Leu Val Asn His Asn Ser Val Phe Lys Thr His Leu Leu Pro Gln Thr
            20                  25                  30

Gly Phe Pro Glu Asp Gln Leu Ser Leu Ser Asp Gln Gln Ile Leu Ser
        35                  40                  45

Ser Arg Gln Gly His Leu Asp Arg Ser Phe Thr Cys Ser Thr Arg Ser
    50                  55                  60

Ala Ala Tyr Asn Pro Ser Tyr Tyr Ser Asp Asn Pro Ser Ser Asp Ser
65                  70                  75                  80

Phe Leu Gly Ser Gly Asp Leu Arg Thr Phe Gly Gln Ser Ala Asn Gly
                85                  90                  95

Gln Trp Arg Asn Ser Thr Pro Ser Ser Ser Ser Leu Gln Lys Ser
            100                 105                 110

Arg Asn Ser Arg Ser Leu Tyr Leu Glu Thr Arg Lys Thr Ser Ser Gly
        115                 120                 125

Leu Ser Asn Ser Phe Ala Gly Lys Ser Asn His His Cys His Val Ser
    130                 135                 140

Ala Tyr Glu Lys Ser Phe Pro Ile Lys Pro Val Pro Ser Pro Ser Trp
145                 150                 155                 160

Ser Gly Ser Cys Arg Arg Ser Leu Leu Ser Pro Lys Lys Thr Gln Arg
                165                 170                 175

Arg His Val Ser Thr Ala Glu Glu Thr Val Gln Glu Glu Arg Glu
            180                 185                 190

Ile Tyr Arg Gln Leu Leu Gln Met Val Thr Gly Lys Gln Phe Thr Ile
        195                 200                 205

Ala Lys Pro Thr Thr His Phe Pro Leu His Leu Ser Arg Cys Leu Ser
    210                 215                 220

Ser Ser Lys Asn Thr Leu Lys Asp Ser Leu Phe Lys Asn Gly Asn Ser
225                 230                 235                 240

Cys Ala Ser Gln Ile Ile Gly Ser Asp Thr Ser Ser Gly Ser Ala
                245                 250                 255

Ser Ile Leu Thr Asn Gln Glu Gln Leu Ser His Ser Val Tyr Ser Leu
            260                 265                 270

Ser Ser Tyr Thr Pro Asp Val Ala Phe Gly Ser Lys Asp Ser Gly Thr
        275                 280                 285
```

```
Leu His His Pro His His His Ser Val Pro His Gln Pro Asp Asn
    290                 295                 300

Leu Ala Ala Ser Asn Thr Gln Ser Glu Gly Ser Asp Ser Val Ile Leu
305                 310                 315                 320

Leu Lys Val Lys Asp Ser Gln Thr Pro Thr Pro Ser Ser Thr Phe Phe
                325                 330                 335

Gln Ala Glu Leu Trp Ile Lys Glu Leu Thr Ser Val Tyr Asp Ser Arg
            340                 345                 350

Ala Arg Glu Arg Leu Arg Gln Ile Glu Glu Gln Lys Ala Leu Ala Leu
        355                 360                 365

Gln Leu Gln Asn Gln Arg Leu Gln Arg Glu His Ser Val His Asp
    370                 375                 380

Ser Val Glu Leu His Leu Arg Val Pro Leu Glu Lys Glu Ile Pro Val
385                 390                 395                 400

Thr Val Val Gln Glu Thr Gln Lys Lys Gly His Lys Leu Thr Asp Ser
                405                 410                 415

Glu Asp Glu Phe Pro Glu Ile Thr Glu Glu Met Glu Lys Glu Ile Lys
            420                 425                 430

Asn Val Phe Arg Asn Gly Asn Gln Asp Glu Val Leu Ser Glu Ala Phe
        435                 440                 445

Arg Leu Thr Ile Thr Arg Lys Asp Ile Gln Thr Leu Asn His Leu Asn
450                 455                 460

Trp Leu Asn Asp Glu Ile Ile Asn Phe Tyr Met Asn Met Leu Met Glu
465                 470                 475                 480

Arg Ser Lys Glu Lys Gly Leu Pro Ser Val His Ala Phe Asn Thr Phe
                485                 490                 495

Phe Phe Thr Lys Leu Lys Thr Ala Gly Tyr Gln Ala Val Lys Arg Trp
            500                 505                 510

Thr Lys Lys Val Asp Val Phe Ser Val Asp Ile Leu Leu Val Pro Ile
        515                 520                 525

His Leu Gly Val His Trp Cys Leu Ala Val Val Asp Phe Arg Lys Lys
530                 535                 540

Asn Ile Thr Tyr Tyr Asp Ser Met Gly Gly Ile Asn Asn Glu Ala Cys
545                 550                 555                 560

Arg Ile Leu Leu Gln Tyr Leu Lys Gln Glu Ser Ile Asp Lys Lys Arg
                565                 570                 575

Lys Glu Phe Asp Thr Asn Gly Trp Gln Leu Phe Ser Lys Lys Ser Gln
            580                 585                 590

Ile Pro Gln Gln Met Asn Gly Ser Asp Cys Gly Met Phe Ala Cys Lys
        595                 600                 605

Tyr Ala Asp Cys Ile Thr Lys Asp Arg Pro Ile Asn Phe Thr Gln Gln
    610                 615                 620

His Met Pro Tyr Phe Arg Lys Arg Met Val Trp Glu Ile Leu His Arg
625                 630                 635                 640

Lys Leu Leu

<210> SEQ ID NO 3
<211> LENGTH: 9
<212> TYPE: PRT
<213> ORGANISM: Influenza virus

<400> SEQUENCE: 3

Tyr Pro Tyr Asp Val Pro Asp Tyr Ala
  1               5
```

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 4

Arg Gly Ser His His His His
 1               5

<210> SEQ ID NO 5
<211> LENGTH: 28
<212> TYPE: DNA
<213> ORGANISM: Human

<400> SEQUENCE: 5
cattttaact aaccaggaac agctgtcc                                      28

<210> SEQ ID NO 6
<211> LENGTH: 25
<212> TYPE: DNA
<213> ORGANISM: Human

<400> SEQUENCE: 6
caagagtttt cggtggagga tctcc                                         25

<210> SEQ ID NO 7
<211> LENGTH: 2795
<212> TYPE: DNA
<213> ORGANISM: Human

<400> SEQUENCE: 7
accacaaagc ccatggtaac ttctgcttgt aatggaacaa ggaatgtggc cccttcagga     60
gaggtatttt cgaactcttc atcttgtgaa ctgacaggtt ctggatcctg aacaacatg    120 ctgaaactgg gtaataaatc tcctaatgga ataagtgact atccaaagat cagagtgaca    180
gttacccgag atcagccacg cagagtcctg ccttcctttg gttttacttt gaactcagaa    240
ggctgtaata aagaccaggt ggccgtcgc catagcaaag gtaatccaga gagttcttta    300
atgtggaaac tcaggaaca ggctgtaaca gagatgattt ctgaagagag tggcaagggt    360
ctgaggcgtc cccattgtac tgtggaggag ggtgttcaaa agaggaaag agagaagtac    420 cgaaagttat tggaacgact taagaaagt ggtcatggaa actctgtctg tcctgtaact    480
tcaaattatc acagttctca aagaagtcag atggacacat taagaccaa aggctggggg    540 gaagagcaaa atcacggagt caaaacaact cagtttgttc caaacaata tagacttgtt    600 gaaacaaggg gacctctatg ttcattgaga agtgaaaaga ggtgttcaaa ggggaaaatt    660
actgatacag agaagatggt cggaatcaga tttgaaaatg aaagtaggag gggataccaa    720
ctggagcctg acctatcaga agaagtgtcg gcccgactcc gcctgggcag tggaagcaat    780
ggcttactca ggaggaaagt gtcaataatt gagacaaagg aaaagaattg ctcaggcaaa    840
gagagggaca aagaacgga cgatctcctt gaacttacag aggacatgga aaggaaatc    900 agtaatgccc taggccatgg cccacaggat gaaatcctaa gtagtgcttt caaattgcga    960
attactcgag gagatattca gacattaaag aactatcact ggctcaatga tgaagtcatt   1020
aatttttaca tgaatcttct ggtggaaaga aataaaaagc aaggctatcc agcacttcat   1080
gtattcagta ctttcttcta tcctaaatta aagtctgggg gttaccaagc agtgaaacga   1140

-continued

```
tggaccaaag gggtaaatct ctttgaacaa gaaattattc tggtgcctat tcatcggaag    1200
gtacattgga gcctggtggt gattgaccta agaaaaaagt gtcttaaata tctggattct    1260
atgggacaaa agggccacag gatctgtgag attctccttc agtatttaca ggatgaaagt    1320
aagaccaaaa gaaatagtga tctgaatctt ttagagtgga cccatcacag catgaaacca    1380
cacgagattc ctcaacagct gaatgggagt gattgtggaa tgtttacttg taaatatgca    1440
gattatattt ctagggacaa acctatcaca tttactcagc accagatgcc tctcttccgg    1500
aagaagatgg tgtgggaaat ccttcatcag cagttgctgt gagaaaactt tgcctggtcc    1560
ctctagctgc tggtggttct ttcacagaca tttccatata cctcatgcat gtgggttaa     1620
aaagtccctg catcacttct gttctcacag gtactgagct gtcaaaagtg catgaaggcc    1680
tctcactgta ctctagtcct gacttggggt gcagagggct gcttgcaatc ctgtttgtaa    1740
ggctgtgcct gctcagagct ttggactgtt caacccacac aagaacaaac gctaactaat    1800
atttttttta agagattctt ttccctatga atgtgggaaa tgcaggattt attctgtgaa    1860
ttgtttgttt ctgtgtgttt gttcagcgta ttcattcact cactcgtttg caaacataat    1920
gggcagtggt catttactgc tgctctttta cagttagctc taaattactt gtttgaacta    1980
tttatttctg aaaggaatgt tactcaagct gccactccct gctgaagagc aggagggaac    2040
tctcactggg ggcggaagga agtggagctg gagcagtaac tgccaacatg aagctggagg    2100
gtttgggatt tttttttgttt ttgttttttt gaggctcaaa aaatgctggg agaaatgaaa   2160
atgctgtggg ataggggctcc tgttgccttt cagaggaagt ctgacactac agcgttggca    2220
cagtgccgtg aacagtggaa ctgtgcccaa gggactctga ctatccaagc atcttccgaa    2280
gagtgttgtg gtcaccttaa agagacttcc ctttctggaa atgtggtgac ttggcttagt    2340
cttcaaactg gattcatgga tttgaagtaa ctgtaaaccc taaatcttca ttttcatccc    2400
agatctggtt gagtataaac ctcagaattg tagggggctgg cctgagctgt ttatttcaaa    2460
agatactatt caatttaaag ctattttttcc tcagagtttt tgttttctat atattaagtc    2520
taaattaagt tttctactca ttaagactaa catctcccca ctccatcccc actgaaattt    2580
gtggaagaaa atttagtact tggctctgag gttgccagtt atacaataat ctattttgca    2640
tatgaaagtt tgtatttaac ttttttgttc attaaaaacc ttactgatat ggttataact    2700
tcagacagtt tagagttggt cagaacatat tttgcaagat ctagtgccta gtgttgcttt    2760
tctgatgtaa taaaaggtgg tctggcagaa cctaa                              2795
```

<210> SEQ ID NO 8
<211> LENGTH: 509
<212> TYPE: PRT
<213> ORGANISM: Human

<400> SEQUENCE: 8

```
Met Val Thr Ser Ala Cys Asn Gly Thr Arg Asn Val Ala Pro Ser Gly
  1               5                  10                  15

Glu Val Phe Ser Asn Ser Ser Cys Glu Leu Thr Gly Ser Gly Ser
             20                  25                  30

Trp Asn Asn Met Leu Lys Leu Gly Asn Lys Ser Pro Asn Gly Ile Ser
         35                  40                  45

Asp Tyr Pro Lys Ile Arg Val Thr Val Thr Arg Asp Gln Pro Arg Arg
     50                  55                  60

Val Leu Pro Ser Phe Gly Phe Thr Leu Asn Ser Glu Gly Cys Asn Arg
 65                  70                  75                  80
```

-continued

Arg Pro Gly Gly Arg Arg His Ser Lys Gly Asn Pro Glu Ser Ser Leu
                85                  90                  95

Met Trp Lys Pro Gln Glu Gln Ala Val Thr Glu Met Ile Ser Glu Glu
            100                 105                 110

Ser Gly Lys Gly Leu Arg Arg Pro His Cys Thr Val Glu Glu Gly Val
        115                 120                 125

Gln Lys Glu Glu Arg Glu Lys Tyr Arg Lys Leu Leu Glu Arg Leu Lys
    130                 135                 140

Glu Ser Gly His Gly Asn Ser Val Cys Pro Val Thr Ser Asn Tyr His
145                 150                 155                 160

Ser Ser Gln Arg Ser Gln Met Asp Thr Leu Lys Thr Lys Gly Trp Gly
                165                 170                 175

Glu Glu Gln Asn His Gly Val Lys Thr Thr Gln Phe Val Pro Lys Gln
            180                 185                 190

Tyr Arg Leu Val Glu Thr Arg Gly Pro Leu Cys Ser Leu Arg Ser Glu
        195                 200                 205

Lys Arg Cys Ser Lys Gly Lys Ile Thr Asp Thr Glu Lys Met Val Gly
    210                 215                 220

Ile Arg Phe Glu Asn Glu Ser Arg Arg Gly Tyr Gln Leu Glu Pro Asp
225                 230                 235                 240

Leu Ser Glu Glu Val Ser Ala Arg Leu Arg Leu Gly Ser Gly Ser Asn
                245                 250                 255

Gly Leu Leu Arg Arg Lys Val Ser Ile Ile Glu Thr Lys Glu Lys Asn
            260                 265                 270

Cys Ser Gly Lys Glu Arg Asp Arg Arg Thr Asp Asp Leu Leu Glu Leu
        275                 280                 285

Thr Glu Asp Met Glu Lys Glu Ile Ser Asn Ala Leu Gly His Gly Pro
    290                 295                 300

Gln Asp Glu Ile Leu Ser Ser Ala Phe Lys Leu Arg Ile Thr Arg Gly
305                 310                 315                 320

Asp Ile Gln Thr Leu Lys Asn Tyr His Trp Leu Asn Asp Glu Val Ile
                325                 330                 335

Asn Phe Tyr Met Asn Leu Leu Val Glu Arg Asn Lys Lys Gln Gly Tyr
            340                 345                 350

Pro Ala Leu His Val Phe Ser Thr Phe Phe Tyr Pro Lys Leu Lys Ser
        355                 360                 365

Gly Gly Tyr Gln Ala Val Lys Arg Trp Thr Lys Gly Val Asn Leu Phe
    370                 375                 380

Glu Gln Glu Ile Ile Leu Val Pro Ile His Arg Lys Val His Trp Ser
385                 390                 395                 400

Leu Val Val Ile Asp Leu Arg Lys Lys Cys Leu Lys Tyr Leu Asp Ser
                405                 410                 415

Met Gly Gln Lys Gly His Arg Ile Cys Glu Ile Leu Leu Gln Tyr Leu
            420                 425                 430

Gln Asp Glu Ser Lys Thr Lys Arg Asn Ser Asp Leu Asn Leu Leu Glu
        435                 440                 445

Trp Thr His His Ser Met Lys Pro His Glu Ile Pro Gln Gln Leu Asn
    450                 455                 460

Gly Ser Asp Cys Gly Met Phe Thr Cys Lys Tyr Ala Asp Tyr Ile Ser
465                 470                 475                 480

Arg Asp Lys Pro Ile Thr Phe Thr Gln His Gln Met Pro Leu Phe Arg
                485                 490                 495

```
Lys Lys Met Val Trp Glu Ile Leu His Gln Gln Leu Leu
        500                 505
```

<210> SEQ ID NO 9
<211> LENGTH: 2206
<212> TYPE: DNA
<213> ORGANISM: Human

<400> SEQUENCE: 9

| | | | | | |
|---|---|---|---|---|---|
| agccgccttg | gggcccgtcc | gcccggcttc | cccgctcccg | ggtactggaa gatgaaagag | 60 |
| actatacaag | ggaccgggtc | ctgggggcct | gagcctcctg | acccggcac cacttactca | 120 |
| agtcccaggc | gggacggtct | tcgttggccc | ccacccccta | agccccggct caagtccggt | 180 |
| ggtggttttg | ggccagatcc | tgggtctggg | accacagtgc | caactagacg cctccctgcc | 240 |
| ccccggccat | cttttgatgc | ctcagctagt | gaagaagagg | aagaggaaga ggaggaagat | 300 |
| gaggaggaag | tagcagcttg | gaggctaccc | cctaggtggg | gccaactggg ggcctcccag | 360 |
| cgctctcgag | ctctccgacc | ctctcataga | aaaacctgct | cacagcgccg gcgccgagcc | 420 |
| atgagagcct | tccagatgct | gctctactca | aaaagcacct | cgctgacatt ccactggaag | 480 |
| cttttggggc | gccaccgggg | ccggcggcgg | ggcctcgcac | accccaagaa ccatctttca | 540 |
| ccccagcaag | ggggtgcgac | gccacaggtg | ccatcccct | gttgtcgttt tgactccccc | 600 |
| cggggggccac | ctccaccccg | gctgggtctg | ctaggtgctc | tcatggctga ggatgggtg | 660 |
| agagggtctc | caccagtgcc | ctctgggccc | ccatggagg | aagatggact caggtggact | 720 |
| ccaaagtctc | ctctggaccc | tgactcgggc | ctcctttcat | gtactctgcc caacggtttt | 780 |
| gggggacaat | ctgggccaga | aggggagcgc | agcttggcac | cccctgatgc cagcatcctc | 840 |
| atcagcaatg | tgtgcagcat | cggggaccat | gtggcccagg | agcttttca gggctcagat | 900 |
| ttgggcatgg | cagaagaggc | agagaggcct | ggggagaaag | ccggccagca cagccccctg | 960 |
| cgagaggagc | atgtgacctg | cgtacagagc | atcttggacg | aattccttca aacgtatggc | 1020 |
| agcctcatac | ccctcagcac | tgatgaggta | gtagagaagc | tggaggacat tttccagcag | 1080 |
| gagttttcca | cccccttccag | gaaggggctg | gtgttgcagc | tgatccagtc ttaccagcgg | 1140 |
| atgccaggca | atgccatggt | gaggggctcc | gagtggcttt | ataagcggca cgtgctgacc | 1200 |
| atggatgact | tggggaccctt | gtatggacag | aactggctca | atgaccaggt gatgaacatg | 1260 |
| tatggagacc | tggtcatgga | cacagtccct | gaaaaggtgc | atttcttcaa tagtttcttc | 1320 |
| tatgataaac | tccgtaccaa | ggggttatgat | ggggtgaaaa | ggtggaccaa aaacgtggac | 1380 |
| atcttcaata | aggagctact | gctaatcccc | atccacctgg | aggtgcattg gtccctcatc | 1440 |
| tctgttgatg | tgaggcgacg | caccatcacc | tatttgact | cgcagcgtac cctaaaccgc | 1500 |
| cgctgcccta | agcatattgc | caagtatcta | caggcagagg | cggtaaagaa agaccgactg | 1560 |
| gatttccacc | agggctggaa | aggttacttc | aaaatgaatg | tggccaggca gaataatgac | 1620 |
| agtgactgtg | gtgcttttgt | gttgcagtac | tgcaagcatc | tggccctgtc tcagccattc | 1680 |
| agcttcaccc | agcaggacat | gcccaaactt | cgtcggcaga | tctacaagga gctgtgtcac | 1740 |
| tgcaaactca | ctgtgtgagc | ctcgtacccc | agaccccaag | cccataaatg ggaagggaga | 1800 |
| catgggagtc | cctcccaag | aaactccagt | tcctttcctc | tcttgcctct tcccactcac | 1860 |
| ttcccttgg | ttttcatat | ttaaatgttt | caatttctgt | atttttttt ctttgagaga | 1920 |
| atacttgttg | atttctgatg | tgcaggggt | ggctacagaa | aagccccttt cttcctctgt | 1980 |
| ttgcagggga | gtgtggccct | gtggcctggg | tggagcagtc | atcctccccc ttcccgtgc | 2040 |

```
agggagcagg aaatcagtgc tgggggtggt gggcggacaa taggatcact gcctgccaga    2100
tcttcaaact tttatatata tatatatata tatatataaa tatataaaaa tatataaatg    2160
ccacggtcct gctctggtca ataaaggatc ctttgttgat acgtaa                  2206
```

<210> SEQ ID NO 10
<211> LENGTH: 568
<212> TYPE: PRT
<213> ORGANISM: Human

<400> SEQUENCE: 10

```
Met Lys Glu Thr Ile Gln Gly Thr Gly Ser Trp Gly Pro Glu Pro Pro
  1               5                  10                  15

Gly Pro Gly Thr Thr Tyr Ser Ser Pro Arg Arg Asp Gly Leu Arg Trp
                 20                  25                  30

Pro Pro Pro Lys Pro Arg Leu Lys Ser Gly Gly Phe Gly Pro
             35                  40                  45

Asp Pro Gly Ser Gly Thr Val Pro Thr Arg Arg Leu Pro Ala Pro
         50                  55                  60

Arg Pro Ser Phe Asp Ala Ser Ala Ser Glu Glu Glu Glu Glu Glu
 65                  70                  75                  80

Glu Glu Asp Glu Glu Glu Val Ala Ala Trp Arg Leu Pro Pro Arg Trp
                 85                  90                  95

Gly Gln Leu Gly Ala Ser Gln Arg Ser Arg Ala Leu Arg Pro Ser His
                100                 105                 110

Arg Lys Thr Cys Ser Gln Arg Arg Arg Ala Met Arg Ala Phe Gln
            115                 120                 125

Met Leu Leu Tyr Ser Lys Ser Thr Ser Leu Thr Phe His Trp Lys Leu
    130                 135                 140

Trp Gly Arg His Arg Gly Arg Arg Gly Leu Ala His Pro Lys Asn
145                 150                 155                 160

His Leu Ser Pro Gln Gln Gly Gly Ala Thr Pro Gln Val Pro Ser Pro
                165                 170                 175

Cys Cys Arg Phe Asp Ser Pro Arg Gly Pro Pro Pro Arg Leu Gly
                180                 185                 190

Leu Leu Gly Ala Leu Met Ala Glu Asp Gly Val Arg Gly Ser Pro Pro
                195                 200                 205

Val Pro Ser Gly Pro Pro Met Glu Glu Asp Gly Leu Arg Trp Thr Pro
    210                 215                 220

Lys Ser Pro Leu Asp Pro Asp Ser Gly Leu Leu Ser Cys Thr Leu Pro
225                 230                 235                 240

Asn Gly Phe Gly Gly Gln Ser Gly Pro Glu Gly Glu Arg Ser Leu Ala
                245                 250                 255

Pro Pro Asp Ala Ser Ile Leu Ile Ser Asn Val Cys Ser Ile Gly Asp
            260                 265                 270

His Val Ala Gln Glu Leu Phe Gln Gly Ser Asp Leu Gly Met Ala Glu
    275                 280                 285

Glu Ala Glu Arg Pro Gly Glu Lys Ala Gly Gln His Ser Pro Leu Arg
    290                 295                 300

Glu Glu His Val Thr Cys Val Gln Ser Ile Leu Asp Glu Phe Leu Gln
305                 310                 315                 320

Thr Tyr Gly Ser Leu Ile Pro Leu Ser Thr Asp Glu Val Val Glu Lys
                325                 330                 335

Leu Glu Asp Ile Phe Gln Gln Glu Phe Ser Thr Pro Ser Arg Lys Gly
                340                 345                 350
```

-continued

```
Leu Val Leu Gln Leu Ile Gln Ser Tyr Gln Arg Met Pro Gly Asn Ala
        355                 360                 365

Met Val Arg Gly Phe Arg Val Ala Tyr Lys Arg His Val Leu Thr Met
        370                 375                 380

Asp Asp Leu Gly Thr Leu Tyr Gly Gln Asn Trp Leu Asn Asp Gln Val
385                     390                 395                 400

Met Asn Met Tyr Gly Asp Leu Val Met Asp Thr Val Pro Glu Lys Val
                405                 410                 415

His Phe Phe Asn Ser Phe Phe Tyr Asp Lys Leu Arg Thr Lys Gly Tyr
            420                 425                 430

Asp Gly Val Lys Arg Trp Thr Lys Asn Val Asp Ile Phe Asn Lys Glu
        435                 440                 445

Leu Leu Leu Ile Pro Ile His Leu Glu Val His Trp Ser Leu Ile Ser
        450                 455                 460

Val Asp Val Arg Arg Arg Thr Ile Thr Tyr Phe Asp Ser Gln Arg Thr
465                 470                 475                 480

Leu Asn Arg Arg Cys Pro Lys His Ile Ala Lys Tyr Leu Gln Ala Glu
                485                 490                 495

Ala Val Lys Lys Asp Arg Leu Asp Phe His Gln Gly Trp Lys Gly Tyr
            500                 505                 510

Phe Lys Met Asn Val Ala Arg Gln Asn Asn Asp Ser Asp Cys Gly Ala
        515                 520                 525

Phe Val Leu Gln Tyr Cys Lys His Leu Ala Leu Ser Gln Pro Phe Ser
        530                 535                 540

Phe Thr Gln Gln Asp Met Pro Lys Leu Arg Arg Gln Ile Tyr Lys Glu
545                 550                 555                 560

Leu Cys His Cys Lys Leu Thr Val
                565
```